(12) United States Patent
Luke et al.

(10) Patent No.: US 12,053,463 B2
(45) Date of Patent: *Aug. 6, 2024

(54) SOLID FORMS OF ((S)-5-((1-(6-CHLORO-2-OXO-1,2-DIHYDROQUINOLIN-3-YL)ETHYL) AMINO)-1-METHYL-6-OXO-1,6-DIHYDROPYRIDINE-2-CARBONITRILE

(71) Applicant: FORMA Therapeutics, Inc., Watertown, MA (US)

(72) Inventors: George P. Luke, Clinton, CT (US); Pratik Sheth, Watertown, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/215,727

(22) Filed: Jun. 28, 2023

(65) Prior Publication Data

US 2024/0033261 A1    Feb. 1, 2024

Related U.S. Application Data

(63) Continuation of application No. 17/183,606, filed on Feb. 24, 2021, now Pat. No. 11,723,905, which is a continuation of application No. 16/693,642, filed on Nov. 25, 2019, now Pat. No. 10,959,994, which is a continuation of application No. 16/414,716, filed on May 16, 2019, now Pat. No. 10,532,047.

(60) Provisional application No. 62/692,591, filed on Jun. 29, 2018, provisional application No. 62/672,461, filed on May 16, 2018, provisional application No. 62/672,462, filed on May 16, 2018.

(51) Int. Cl.
| | |
|---|---|
| *A61K 31/4709* | (2006.01) |
| *A61K 9/00* | (2006.01) |
| *A61K 47/12* | (2006.01) |
| *A61K 47/38* | (2006.01) |

(52) U.S. Cl.
CPC ........ *A61K 31/4709* (2013.01); *A61K 9/0053* (2013.01); *A61K 47/12* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,262,564 A | 11/1993 | Kun et al. | |
| 5,984,882 A | 11/1999 | Rosenschein et al. | |
| 6,410,516 B1 | 6/2002 | Baltimore et al. | |
| 6,914,128 B1 | 7/2005 | Salfeld et al. | |
| 6,979,675 B2 | 12/2005 | Tidmarsh | |
| 7,217,286 B2 | 5/2007 | Falotico et al. | |
| 8,367,347 B2 | 2/2013 | Hartmann et al. | |
| 8,469,749 B2 | 6/2013 | Ladouceur et al. | |
| 8,685,660 B2 | 4/2014 | Vogelstein et al. | |
| 8,876,991 B2 | 11/2014 | Luebke | |
| 8,882,892 B2 | 11/2014 | Hoversten et al. | |
| 8,883,438 B2 | 11/2014 | Cantley et al. | |
| 8,933,395 B2 | 1/2015 | Mueth et al. | |
| 9,073,941 B2 | 7/2015 | Wong et al. | |
| 9,335,332 B2 | 5/2016 | Kumaravel et al. | |
| 9,353,418 B2 | 5/2016 | Vogelstein et al. | |
| 9,624,175 B2 | 4/2017 | Lin et al. | |
| 9,624,216 B2 | 4/2017 | Lin et al. | |
| 9,771,349 B2 | 9/2017 | Lin et al. | |
| 9,815,817 B2 | 11/2017 | Lin et al. | |
| 9,834,539 B2 | 12/2017 | Lin et al. | |
| 10,005,734 B2 | 6/2018 | Lin et al. | |
| 10,253,015 B2 | 4/2019 | Lin et al. | |
| 10,266,495 B2 | 4/2019 | Lin et al. | |
| 10,280,150 B2 | 5/2019 | Lin et al. | |
| 10,414,752 B2 | 9/2019 | Lin et al. | |
| 10,532,047 B2 * | 1/2020 | Luke | A61K 47/38 |
| 10,550,098 B2 | 2/2020 | Lin et al. | |
| 10,610,125 B2 | 4/2020 | Dang et al. | |
| 10,704,108 B2 | 7/2020 | Vogelstein et al. | |
| 10,837,064 B2 | 11/2020 | Vogelstein et al. | |
| 10,959,994 B2 * | 3/2021 | Luke | A61K 9/0053 |
| 11,497,743 B2 | 11/2022 | Kelly et al. | |
| 11,498,913 B2 | 11/2022 | Lin et al. | |
| 2003/0105124 A1 | 6/2003 | Sobolov-Jaynes | |
| 2004/0106645 A1 | 6/2004 | Blackburn et al. | |
| 2006/0281122 A1 | 12/2006 | Bryant et al. | |
| 2008/0300208 A1 | 12/2008 | Einat et al. | |
| 2012/0184548 A1 | 7/2012 | Dominique et al. | |
| 2012/0184562 A1 | 7/2012 | Luk | |
| 2014/0235620 A1 | 8/2014 | Caferro et al. | |
| 2016/0083349 A1 | 3/2016 | Lin et al. | |
| 2016/0083365 A1 | 3/2016 | Lin et al. | |
| 2016/0083366 A1 | 3/2016 | Lin et al. | |
| 2016/0083367 A1 | 3/2016 | Lin et al. | |
| 2016/0311774 A1 | 10/2016 | Lin et al. | |

(Continued)

FOREIGN PATENT DOCUMENTS

| | | |
|---|---|---|
| CN | 102558049 A | 7/2012 |
| CN | 103814020 A | 5/2014 |

(Continued)

OTHER PUBLICATIONS

U.S. Appl. No. 17/055,278, filed Jul. 1, 2021, Kelly et al.

(Continued)

*Primary Examiner* — Brian J Davis

(74) *Attorney, Agent, or Firm* — Travis Young; Bozicevic, Field & Francis LLP

(57) ABSTRACT

The present disclosure reports solid forms of ((S)-5-((1-(6-chloro-2-oxo-1,2-dihydroquinolin-3-yl)ethyl)amino)-1-methyl-6-oxo-1,6-dihydropyridine-2-carbonitrile.

13 Claims, 4 Drawing Sheets

(56) References Cited

U.S. PATENT DOCUMENTS

| | | |
|---|---|---|
| 2016/0311818 A1 | 10/2016 | Lin et al. |
| 2017/0081730 A1 | 3/2017 | Vogelstein et al. |
| 2017/0157132 A1 | 6/2017 | Wu et al. |
| 2017/0174658 A1 | 6/2017 | Lin et al. |
| 2018/0086733 A1 | 3/2018 | Lin et al. |
| 2018/0118732 A1 | 5/2018 | Lin et al. |
| 2018/0134682 A1 | 5/2018 | Lin et al. |
| 2018/0141910 A1 | 5/2018 | Lin et al. |
| 2018/0312487 A1 | 11/2018 | Lin et al. |
| 2018/0327361 A1 | 11/2018 | Lin et al. |
| 2018/0327382 A1 | 11/2018 | Lin et al. |
| 2019/0135781 A1 | 5/2019 | Lin et al. |
| 2019/0263778 A1 | 8/2019 | Lin et al. |
| 2019/0350919 A1 | 11/2019 | Kelly et al. |
| 2019/0350920 A1 | 11/2019 | Luke et al. |
| 2019/0350921 A1 | 11/2019 | Ashwell |
| 2019/0350922 A1 | 11/2019 | Kelly et al. |
| 2020/0085815 A1 | 3/2020 | Luke et al. |
| 2020/0108060 A1 | 4/2020 | Kelly et al. |
| 2020/0223822 A1 | 7/2020 | Lin et al. |
| 2020/0297717 A1 | 9/2020 | Kelly et al. |
| 2021/0196701 A1 | 7/2021 | Kelly et al. |

FOREIGN PATENT DOCUMENTS

| | | |
|---|---|---|
| EP | 0481802 A1 | 4/1992 |
| RU | 2284325 C2 | 9/2006 |
| WO | WO-00/40749 A2 | 7/2000 |
| WO | WO-2006/054912 A1 | 5/2006 |
| WO | WO-2007/117778 A2 | 10/2007 |
| WO | WO-2008/010964 A1 | 1/2008 |
| WO | WO-2008/069242 A1 | 6/2008 |
| WO | WO-2010/028099 A1 | 3/2010 |
| WO | WO-2010/105243 A1 | 9/2010 |
| WO | WO-2011/050210 A1 | 4/2011 |
| WO | WO-2011/050211 A2 | 4/2011 |
| WO | WO-2011/072174 A1 | 6/2011 |
| WO | WO-2012/040332 A2 | 3/2012 |
| WO | WO-2012/054915 A2 | 4/2012 |
| WO | WO-2012/079532 A1 | 6/2012 |
| WO | WO-2012/129562 A2 | 9/2012 |
| WO | WO-2012/171337 A1 | 12/2012 |
| WO | WO-2012/171506 A1 | 12/2012 |
| WO | WO-2012/173682 A2 | 12/2012 |
| WO | WO-2013/046136 A1 | 4/2013 |
| WO | WO-2013/096820 A1 | 6/2013 |
| WO | WO-2013/102431 A1 | 7/2013 |
| WO | WO-2013/107291 A1 | 7/2013 |
| WO | WO-2013/107405 A1 | 7/2013 |
| WO | WO-2013/127997 A1 | 9/2013 |
| WO | WO-2014/141153 A1 | 9/2014 |
| WO | WO-2014/147586 A1 | 9/2014 |
| WO | WO-2014/184272 A2 | 11/2014 |
| WO | WO-2015/003146 A1 | 1/2015 |
| WO | WO-2015/121210 A1 | 8/2015 |
| WO | WO-2016/044781 A1 | 3/2016 |
| WO | WO-2016/044782 A1 | 3/2016 |
| WO | WO-2016/044787 A1 | 3/2016 |
| WO | WO-2016/044789 A1 | 3/2016 |
| WO | WO-2016/106331 A1 | 6/2016 |
| WO | WO-2016/108045 A2 | 7/2016 |
| WO | WO-2016/171755 A1 | 10/2016 |
| WO | WO-2016/171756 A1 | 10/2016 |
| WO | WO-2017/019429 A1 | 2/2017 |
| WO | WO-2017/146795 A1 | 8/2017 |
| WO | WO-2017/213910 A1 | 12/2017 |
| WO | WO-2017/223202 A1 | 12/2017 |
| WO | WO-2018/111707 A1 | 6/2018 |
| WO | WO-2019/222551 A1 | 11/2019 |
| WO | WO-2019/222553 A1 | 11/2019 |
| WO | WO-2020/232381 A1 | 11/2020 |

OTHER PUBLICATIONS

A Study of FT-2012 in Patients with Advanced Solid Tumors and Gliomas, Spanish Clinical Studies Registry, retrieved from https://reec.aemps.es/reec/public/detail.html, 16 pages | (2019).

Abbas, S. et al., Acquired mutations in the genes encoding IDH1 and IDH2 both are recurrent aberrations in acute myeloid leukemia: prevalence and prognostic value, Blood, 116(12): 2122-2126 (2010).

Abbott Molecular Inc., Summary of Safety and Effectiveness Data (SSED), 43 pages (2018). URL: <https://www.accessdata.fda.gov/cdrh_docs/pdf17/P170041B.pdf> [Retrieved Jul. 28, 2020].

Abbott Molecular Inc., U.S. Food and Drug Administration Approval Letter, 4 pages (2018). URL: https://www.accessdata.fda.gov/cdrh docs/pdf17/P170041A.pdf.

Abbott RealTime IDH1 label, Reference No. 08N90-090, 31 pages (Jul. 2018); accessed on Jul. 29, 2019 from https://www.fda.gov/medical-devices/vitro-diagnostics/list-cleared-or- approved-companion-diagnostic-devices-vitro-and-imaging-tools.

AbbVie, AbbVie Receives EMA and FDA Orphan Drug Designation for Investigational Compound ABT-414 in the Treatment of Glioblastoma Multiforme, 4 pages (Aug. 4, 2014). URL: https://www.prnewswire.com/news-releases/abbvie-receives-ema-and-fda-orphan-drug- designation-for-investigational-compound-abt-414-in-the-treatment-of-glioblastoma-multiforme-269807321.html.

AbbVie, AbbVie Receives U.S. FDA Rare Pediatric Disease Designation for Investigational ABT-414 for the Treatment of a Type of Pediatric Brain Tumor known as Diffuse Intrinsic Pontine Glioma (DIPG), 3 pages (Jul. 11, 2016). URL: https://news.abbvie.com/article print.cfm?article id=11360.

Aghili, M. et al., Hydroxyglutaric aciduria and malignant brain tumor: a case report and literature review, J. Neurooncol., 91: 233-236 (2009).

Agios Pharmaceuticals, Press Release, Agios Announces Initiation of Phase 1/2 Frontline Combination Study of AG-221 or AG-120 with VIDAZA® (azacitidine for injection) in Newly Diagnosed Acute Myeloid Leukemia (AML) Patients Not Eligible for Intensive Chemotherapy, 4 | paqes (Cambridge, Mass, Mar. 30, 2016).

Agios Pharmaceuticals, Press Release, Agios Announces Phase 1 Data from Dose Expansion Cohorts of AG-120 in Patients with IDH1 Mutant Positive Glioma and Chondrosarcoma, 4 pages (Cambridge, Mass, Nov. 18, 2016).

Agios Pharmaceuticals, Press Release, Agios Pharmaceuticals to Present Clinical and Preclinical Data at the 2014 American Society of Hematology Annual Meeting, 7 pages (Cambridge, Mass., Nov. 6, 2014). URL: <http://investor.agios.com/news-releases/news- release-details/agios-pharmaceuticals-present-clinical-and-preclinical-data-2014> [Retrieved May 14, 2019].

Agios Pharmaceuticals, Press Release, Agios Presents Phase 1 Data from Dose-Escalation and Expansion Cohorts of AG-120 (Ivosidenib) in Patients with Previously Treated IDH1 Mutant Positive Cholangiocarcinoma, 4 pages (Chicago, Jun. 3, 2017).

Agios Pharmaceuticals, Press Release, Agios Presents Updated Data from Phase 1 Dose-Escalation Study of AG-881 in Patients with IDH Mutant Positive Advanced Glioma, 6 pages (Nov. 16, 2018). URL: https://investor.agios.com/news-releases/news-release- details/aqios-presents-updated-data-phase-1-dose-escalation-study-aq-881.

Agios Pharmaceuticals, Press Release, Agios to Present New Data From Lead Programs at the 2015 ASH Annual Meeting, 6 pages (Cambridge, Mass., Nov. 5, 2014). URL: <http://investor.agios.com/news-releases/news-release-details/agios-present-new-data-lead- | programs-2015-ash-annual-meeting> [Retrieved May 14, 2019].

Agios Pharmaceuticals, Press Release, Celgene and Agios Announce Collaborations with Abbott for Diagnostic Identification of IDH Mutations in AML, 4 pages (Summit, N.J. and Cambridge, Mass., Oct. 12, 2016). URL: <https://investor.agios.com/news-releases/news- release-details/celgene-and-agios-announce-collaborations-abbott-diagnostic> [Retrieved Jul. 28, 2020].

Agios Pharmaceuticals, Press Release, FDA Accepts New Drug Application and Grants Priority Review for Ivosidenib in Relapsed or Refractory AML with an IDH1 Mutation, 4 pages (Summit, N.J. and Cambridge, Mass., Feb. 15, 2018). URL: <https://investor.agios.com/news-releases/news-release-details/fda-accepts-new-drug-application-and-grants-priority-review-0> [Retrieved Jul. 28, 2020].

(56) References Cited

OTHER PUBLICATIONS

Agios Pharmaceuticals, Press Release, FDA Grants Approval of TIBSOVO®, the First Oral, Targeted Therapy for Adult Patients with Relapsed/Refractory Acute Myeloid Leukemia and an IDH1 Mutation, 9 pages (Jul. 20, 2018). URL: <https://investor.agios.com/news-releases/news-release-details/fda-grants-approval-tibsovor-first-oral-targeted-therapy-adult> | [Retrieved Jul. 28, 2020].
Agios Pharmaceuticals, Third Quarter 2018 Financial Results, 27 pages (Nov. 1, 2018).
Agios Pharmaceuticals, TIBSOVO® (ivosidenib) FDA Approval, 17 pages (Jul. 20, 2018).
Amary, M.F. et al., IDH1 and IDH2 mutations are frequent events in central chondrosarcoma and central and periosteal chondromas but not in other mesenchymal tumours, J Pathol, 224: 334-343 (2011).
Amary, M.F. et al., Oilier disease and Maffucci syndrome are caused by somatic mosaic mutations ofiDH1 and IDH2, Nature Genetics, 43(12): 1262-1265 (2011).
Amidon, G.L. et al., A Theoretical Basis for a Biopharmaceutical Drug Classification: The Correlation of in Vitro Drug Product Dissolution and in Vivo Bioavailability, Pharmaceutical Research, 12(3): 413-420 (1995).
Androues, O.C. et al., Pharmacodynamics of mutant-IDH1 inhibitors in glioma patients probed by in vivo 3D MRS imaging of2-hydroxyglutarate, Nature Communications, 9: 1474,9 | pages (2018).
Asteian, A. et al., Design, Synthesis, and Biological Evaluation of Indole Biphenylcarboxylic Acids as PPAR? Antagonists, ACS Med. Chem. Lett., 6: 998-1003 (2015).
Badr, M.Z.A. et al., Reaction of Quinoxaline Derivatives with Nucleophilic Reagents, Bull Chem Soc Jpn, 56(1): 326-330 (1983).
Baer, M.R. et al., A Phase 1 Dose Escalation Study of the IDH1m Inhibitor, FT-2102, in Patients with Acute Myeloid Leukemia (AML) or Myelodysplastic Syndrome (MDS), Abstract for Congress of EHA, EHA-1757: 1 page (Jun. 2018).
Baer, M.R. et al., A Phase 1 Dose Escalation Study of the IDH1m Inhibitor, FT-2102, in Patients with Acute Myeloid Leukemia (AML) or Myelodysplastic Syndrome (MDS), Presented at the 2018 Congress of EHA, Poster PF236, Stockholm (Jun. 15, 2018).
Bai, H. et al., Integrated genomic characterization of IDH1-mutant glioma malignant progression, Nature Genetics, 48(1): 59-66 (2016).
Balss, J. et al., Analysis of the IDH1 codon 132 mutation in brain tumors, Acta Neuropathol, 116: 597-602 (2008).
Bayer, Interim Report Third Quarter of 2018, 61 pages (2018).
Bertus, P. and Szymoniak, J., A direct synthesis of 1-aryl- and 1-alkenylcyclopropylamines from aryl and alkenyl Nitriles Journal of Organic Chemistry, 68(18):7133-7136 (2003).
Birendra, K.C. and Dinardo, C.D., Evidence for clinical differentiation and differentiation syndrome in patients with acute myeloid leukemia and IDH1 mutations treated with the targeted mutant IDH1 inhibitor, AG-120, Clin Lymphoma Myeloma Leuk., 16(8): 460-465 (2016).
Blackburn, C. et al., Identification and characterization of aminopiperidinequinolones and quinazolinones as MCHr1 antagonists, Bio. and Med. Chem. Letters, 16(10):2621-2627 (2006).
Bleeker, F.E. et al., IDH1R$^{132}$ mutations occur frequently in high-grade gliomas but not in other solid tumors, Human Mutation, 30:84-91 (2009).
Bleeker, F.E. et al., Recent advances in the molecular understanding of glioblastoma, J. Neurooncol, 108: 11-27 (2012).
Boddu, P. and Borthakur, G., Therapeutic targeting of isocitrate dehydrogenase mutant AML, Expert Opinion on Investigational Drugs, 26(5): 525-529 (2017).
Borg, G. et al., One-pot asymmetric synthesis of tert-butanesulfinyl-protected amines from ketones by the in situ reduction of tert-butanesulfinyl ketimines, Tetrahedron Letters, 40: 6709-6712 (1999).
Borger, D.R. et al., Circulating Oncometabolite 2-Hydroxyglutarate Is a Potential Surrogate Biomarker in Patients with Isocitrate Dehydrogenase-Mutant Intrahepatic Cholangiocarcinoma, Clin Cancer Res, 20(7): 1884-1890 (2014).

Borger, D.R., et al., Frequent mutation of isocitrate dehydrogenase (IDH)1 and IDH2 in cholangiocarcinoma identified through broad-based tumor genotyping, The Oncologist 17, 72-79 (2012).
Borodovsky, A. et al., 5-azacytidine reduces methylation, promotes differentiation and induces tumor regression in a patient-derived IDH1 mutant glioma xenograft, Oncotarget, 4(10): 1737-1747 (2013).
Brooks, E. et al., Identification and Characterization of Small-Molecule Inhibitors of the R132H/R132H Mutant Isocitrate Dehydrogenase 1 Homodimer and R132H!Wild-Type Heterodimer, Journal of Biomolecular Screening, 19(8): 1193-1200 (2014).
Bunse, L. et al., Suppression of antitumor T cell immunity by the oncometabolite (R)-2-hydroxyglutarate, Nature Medicine, 25 pages (2018).
Burris, H. et al., Abstract PL04-05: The first reported results of AG-120, a first-in-class, potent inhibitor of the IDH1 mutant protein, in a Phase I study of patients with advanced IDH1-mutant solid tumors, including gliomas, Mol. Cancer Ther., 14(12 Supplement 2): 5 pages (Dec. 2015).
Caira, M.R. et al., Crystalline polymorphism of organic compounds, Topics in Current Chemistry, 198: 163-208 (1998).
Cairns, R.A. and Mak, T.W., Oncogenic Isocitrate Dehydrogenase Mutations: Mechanisms, Models, and Clinical Opportunities, Cancer Discover, 730-741 (2013).
Cancer Genome Atlas Research Network, Comprehensive, Integrative Genomic Analysis of Diffuse Lower-Grade Gliomas, N Engl J Med, 372: 2481-2498 (2015).
Caravella, J. A. et al., Structure-based design and identification of FT-2102 (olutasidenib), a potent mutant-selective IDH1 inhibitor, J Med Chem, doi: 10.1021/acs.jmedchem.9b01423, Epub ahead of print (2020).
Center for Drug Evaluation and Research, Application No. 2096060rig11000, Multi-Discipline Review, Reference ID: 4131433, 190 pages (Submission date Dec. 30, 2016).
Center for Drug Evaluation and Research, Application No. 2111920rig1s000, Multi-Discipline Review, Reference ID: 4294809, 235 pages (Submission date Dec. 21, 2017).
Chaturvedi, A. et al., Mutant IDH1 promotes leukemogenesis in vivo and can be specifically targeted in human AML, Blood, 122(16): 2877-2887 (2013).
Chaturvedi, A. et al., Pan-mutant-IDH1 inhibitor BAY1436032 is highly effective against human IDH1 mutant acute myeloid leukemia in vivo, Leukemia, 31: 2020-2028 (2017).
Chiou, W.L., and Barve, A., Linear Correlation of the Fraction of Oral Dose Absorbed of64 Drugs Between Humans and Rats, Pharmaceutical Research, 15(11): 1792-1795 (1998).
Cho, Y.S. et al., Discovery and Evaluation of Clinical Candidate IDH305, a Brain Penetrant Mutant IDH1 Inhibitor, ACS Med Chem Lett., 8(10): 1116-1121 (2017). Supporting Information, 31 pages.
Chowdhury, R. et al., The oncometabolite 2-hydroxyglutarate inhibits histone lysine demethylases, EMBO Reports, 12(5): 463-469 (2011).
Claus, E.B. et al., Survival and low-grade glioma: the emergence of genetic Information, Neurosurg Focus, 38(1): E6, 19 pages (2015).
ClinicaiTrials.gov Identifier: NCT00900224, Studying Tissue and Blood Samples From Patients with Acute Myeloid Leukemia, (v40 dated Dec. 15, 2010; update posted Dec. 16, 2010) URL: <https://clinicaltrials.gov/ct2/history/NCT00900224?V 40=View>.
ClinicaiTrials.gov Identifier: NCT01800695, Evaluating the Safety and Pharmacokinetics of ABT-414 for Subjects With Glioblastoma Multiforme (First Posted Feb. 28, 2013, Last Update Posted Nov. 21, 2017). URL: https://clinicaltrials.gov/ct2/show/NCT01800695.
ClinicaiTrials.gov Identifier: NCT02073994, Study of Orally Administered AG-120 in Subjects With Advanced Solid Tumors, Including Glioma, With an IDH1 Mutation (First Posted Feb. 28, 2014, Last Update Posted Dec. 9, 2020). URL: https://clinicaltrials.gov/ct2/show/NCT02073994.
ClinicaiTrials.gov Identifier: NCT02073994, Study of Orally Administered AG-120 in Subjects With Advanced Solid Tumors, Including Glioma, With an IDH1 Mutation, First Posted Feb. 28, 2014; Last Update Posted Jun. 4, 2019. https://clinicaltrials.gov/ct2/show/NCT02073994?term=NCT02073994&rank=1.
ClinicaiTrials.gov Identifier: NCT02074839, Study of Orally Administered AG-120 in Subjects With Advanced Hematologic Malignan-

(56) References Cited

OTHER PUBLICATIONS cies With an IDH1 Mutation (First Posted Feb. 28, 2014, Last Update Posted Feb. 5, 2020). URL: https://clinicaltrials.gov/ct2/show/NCT02074839?term=NCT02074839&draw=2&rank=1.
ClinicaiTrials.gov Identifier: NCT02193347, IDH1 Peptide Vaccine for Recurrent Grade II Glioma (RESIST) (First Posted Jul. 17, 2014, Last Update Posted May 13, 2020). URL: https://clinicaltrials.gov/ct2/show/NCT02193347.
ClinicaiTrials.gov Identifier: NCT02481154, Study of Orally Administered AG-881 in Patients With Advanced Solid Tumors, Including Gliomas, With an IDH1 and/or IDH2 Mutation (First Posted Jun. 25, 2015, Last Update Posted Dec. 17, 2020). URL: https://clinicaltrials.gov/ct2/show/NCT02481154.
ClinicaiTrials.gov Identifier: NCT02481154, Study of Orally Administered AG-881 in Patients With Advanced Solid Tumors, Including Gliomas, With an IDH1 and/or IDH2 Mutation, First Posted Jun. 25, 2015; Last Update Posted Jun. 6, 2019. https://clinicaltrials.gov/ct2/show/NCT02481154?term=NCT02481154&rank=1.
ClinicaiTrials.gov Identifier: NCT02492737, Study of Orally Administered AG-881 in Patients With Advanced Hematologic Malignancies With an IDH1 and/or IDH2 Mutation (First Posted Jul. 9, 2015, Last Update Posted Mar. 8, 2019). URL: https://clinicaltrials.gov/ct2/show/NCT02492737?term=NCT02492737&draw=2&rank=1.
ClinicaiTrials.gov Identifier: NCT02511405, A Phase 3, Pivotal Trial of VB-111 Plus Bevacizumab vs. Bevacizumab in Patients With Recurrent Glioblastoma (GLOBE) (GLOBE) (First Posted Jul. 30, 2015, Last Update Posted Oct. 23, 2018). URL: https://clinicaltrials.gov/ct2/show/NCT02511405?term=VB-111.
ClinicaiTrials.gov Identifier: NCT02573324, A Study of ABT-414 in Participants With Newly Diagnosed Glioblastoma (GBM) With Epidermal Growth Factor Receptor (EGFR) Amplification (Intellance1) (First Posted Oct. 9, 2015, Last Update Posted Dec. 21, 2020). URL: https://clinicaltrials.gov/ct2/show/NCT02573324?term=ABT-414&rank=6.
ClinicaiTrials.gov Identifier: NCT02677922, A Safety and Efficacy Study of Oral AG-120 Plus Subcutaneous Azacitidine and Oral AG-221 Plus Subcutaneous Azacitidine in Subjects With Newly Diagnosed Acute Myeloid Leukemia (AML) (First Posted Feb. 9, 2016, Last Update Posted Dec. 20, 2019). URL: https://clinicaltrials.gov/ct2/show/NCT02677922.
ClinicaiTrials.gov Identifier: NCT02719574, "Open-label Study of FT-2102 With or Without Azacitidine or Cytarabine in Patients With AML or MDS With an IDH1 Mutation," (v1 dated Mar. 21, 2016, published Mar. 24, 2016, and first posted Mar. 25, 2016 at https://clinicaltrials.gov/ct2/history/NCT02719574?V1=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v10 dated Nov. 6, 2017, published Nov. 7, 2017, and update posted Nov. 8, 2017 at https://clinicaltrials.gov/ct2/history/NCT02719574?V1O=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v11 dated Dec. 6, 2017, published Dec. 7, 2017, and update posted Dec. 8, 2017 at https://clinicaltrials.gov/ct2/history/NCT02719574?V11=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v12 dated May 17, 2018, Published May 18, 2018, and update posted May 21, 2018 at https://clinicaltrials.gov/ct2/history/NCT02719574?V12=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v13 dated Nov. 27, 2018, published Nov. 28, 2018, and update posted Nov. 29, 2018 at https://clinicaltrials.gov/ct2/history/NCT02719574?V13=View#StudyPageTop).

ClinicaiTrials.gov Identifier: NCT02719574, "Open-label Study of FT-2102 With or Without Azacitidine or Cytarabine in Patients With AML or MDS With an IDH1 Mutation," (v2 dated Apr. 21, 2016 published Apr. 21, 2016, and update posted Apr. 22, 2016 at https://clinicaltrials.gov/ct2/history/NCT02719574?V2=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v3 dated Jun. 8, 2016, published Jun. 8, 2016, and update posted Jun. 9, 2016 at https://clinicaltrials.gov/ct2/history/NCT02719574?V3=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v4 dated Jul. 1, 2016, published Jul. 1, 2016, and update posted Jul. 4, 2016 at https://clinicaltrials.gov/ct2/history/NCT02719574?V4=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v5 dated Jul. 12, 2016, published Jul. 12, 2016, and update posted Jul. 13, 2016 at https://clinicaltrials.gov/ct2/history/NCT02719574?V5=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v6 dated Aug. 17, 2016, published Aug. 18, 2016, and update posted Aug. 19, 2016 at https://clinicaltrials.qov/ct2/history/NCT02719574?V6=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v7 dated Dec. 8, 2016, published Dec. 8, 2016, and update posted Dec. 9, 2016 at https://clinicaltrials.gov/ct2/history/NCT02719574?V7=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v8 dated Feb. 15, 2017, published Feb. 16, 2017, and update posted Feb. 16, 2017 at https://clinicaltrials.gov/ct2/history/NCT02719574?VB=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," (v9 dated May 5, 2017, published May 5, 2017, and update posted May 8, 2017 at https://clinicaltrials.gov/ct2/history/NCT02719574?V9=View#StudyPageTop).
ClinicaiTrials.gov Identifier: NCT02719574, "Open-label Study of FT-2102 With or Without Azacitidine or Cytarabine in Patients With AML or MDS With an IDH1 Mutation," Trial record 1 of 2 for: FT-2102, Study Details, (First Posted Mar. 25, 2016. Last Update Posted Nov. 29, 2018).
ClinicaiTrials.gov Identifier: NCT02746081, Phase I Study of BAY1436032 in IDH1-mutant Advanced Solid Tumors (First Posted Apr. 21, 2016, Last Update Posted Dec. 22, 2020). URL: https://clinicaltrials.gov/ct2/show/NCT02746081.
ClinicaiTrials.gov Identifier: NCT02771301, Safety and Efficacy of IDH1R132H-DC Vaccine in Gliomas (First Posted May 13, 2016, Last Update Posted May 13, 2016). URL: https://clinicaltrials.gov/ct2/show/NCT02771301.
ClinicaiTrials.gov Identifier: NCT02989857, Study of AG-120 in Previously Treated Advanced Cholangiocarcinoma With IDH1 Mutations (CiariDHy) (CiariDHy) (First Posted Dec. 12, 2016, Last Update Posted Dec. 1, 2020). URL: https://clinicaltrials.gov/ct2/show/NCT02989857.
ClinicaiTrials.gov Identifier: NCT03030066, Study of DS-1001bin Patients With Gene IDH1-Mutated Gliomas (First Posted Jan. 24, 2017, Last Update Posted Feb. 28, 2020). URL: https://clinicaltrials.gov/ct2/show/NCT03030066.
ClinicaiTrials.gov Identifier: NCT03149575, VAL-083 Phase 3 Study in Temozolomide-Avastin (Bevacizumab) Recurrent GBM (STAR-3) (First Posted May 11, 2017, Last Update Posted Nov. 14, 2019). URL: https://clinicaltrials.gov/ct2/show/NCT03149575?term=VAL-083&rank=6.

(56) References Cited

OTHER PUBLICATIONS

ClinicaiTrials.gov Identifier: NCT03173248, Study of AG-120 (Ivosidenib) vs. Placebo in Combination With Azacitidine in Patients With Previously Untreated Acute Myeloid Leukemia With an IDH1 Mutation (AGILE) (First Posted Jun. 1, 2017, Last Update Posted Dec. 24, 2020). URL: https://www.clinicaltrials.gov/ct2/show/NCT03173248.
ClinicaiTrials.gov Identifier: NCT03343197, Study of AG-120 and AG-881 in Subjects With Low Grade Glioma (First Posted Nov. 17, 2017, Last Update Posted Oct. 5, 2020). URL: https://clinicaltrials.qov/ct2/show/NCT03343197.
ClinicaiTrials.gov Identifier: NCT03343197, Study of AG-120 and AG-881 in Subjects With Low Grade Glioma, First Posted Nov. 17, 2017; Last Update Posted Jul. 23, 2018. https://clinicaltrials.gov/ct2/show/NCT03343197?term=NCT03343197&rank=1.
ClinicaiTrials.gov Identifier: NCT03393000, Safety and Efficacy Study of Trans Sodium Crocetinate (TSC) in Newly Diagnosed Glioblastoma (GBM) Biopsy-Only Subjects (INTACT) (First Posted Jan. 8, 2018, Last Update Posted Jan. 28, 2020). URL: https://clinicaltrials.gov/ct2/show/record/NCT03393000?term=trans+sodium+crocetinate&rank=1&view=record.
ClinicalTrials.gov Identifier: NCT03398655, A Study of VB-111 With Paclitaxel vs Paclitaxel for Treatment of Recurrent Platinum-Resistant Ovarian Cancer (OVAL) (OVAL) (First Posted Jan. 12, 2018, Last Update Posted Jan. 1, 2021). URL: https://clinicaltrials.gov/ct2/show/NCT03398655?term=VB-111.
ClinicaiTrials.gov Identifier: NCT03684811, "A Study of FT-2102 in Participants with Advanced Solid Tumors and Gliomas With an IDH1 Mutation," (v1 dated Sep. 24, 2018; update published on Sep. 25, 2018, and posted on Sep. 26, 2018 https://clinicaltrials.gov/ct2/history/NCT03684811?V1=View#StudyPageTop.
ClinicaiTrials.gov Identifier: NCT03684811, "A Study of FT-2102 in Participants with Advanced Solid Tumors and Gliomas With an IDH1 Mutation," (v2 dated Nov. 12, 2018; update published on Nov. 13, 2018, and posted on Nov. 14, 2018 https://clinicaltrials.gov/ct2/history/NCT03684811?V2=View#StudyPageTop.
ClinicaiTrials.gov Identifier: NCT03684811, "A Study of FT-2102 in Participants with Advanced Solid Tumors and Gliomas With an IDH1 Mutation," (v3 dated Feb. 12, 2019; update published on Feb. 12, 2019 and posted on Feb. 15, 2019 https://clinicaltrials.gov/ct2/history/NCT03684811?V 3=View#StudyPageTop.
ClinicaiTrials.gov Identifier: NCT03684811, "A Study of FT-2102 in Participants with Advanced Solid Tumors and Gliomas With an IDH1 Mutation," (v4 dated Feb. 15, 2019; update published on Feb. 18, 2019, and posted on Feb. 19, 2019 https://clinicaltrials.gov/ct2/history/NCT03684811?V 4=View#StudyPageTop.
ClinicaiTrials.gov Identifier: NCT03684811, "A Study of FT-2102 in Participants with Advanced Solid Tumors and Gliomas With an IDH1 Mutation," (v5 dated Mar. 13, 2019; update published on Mar. 13, 2019, and posted on Mar. 14, 2019 https://clinicaltrials.gov/ct2/history/NCT03684811?V 5=View#StudyPageTop.
ClinicaiTrials.gov Identifier: NCT03684811, "A Study of FT-2102 in Participants with Advanced Solid Tumors and Gliomas With an IDH1 Mutation," Study Details (First Posted Sep. 26, 2018, Last Update Posted May 1, 2019).
Cohen, A. et al., IDH1 and IDH2 Mutations in Gliomas, Curr Neural Neurosci Rep., 13(5): 345, 13 pages (2013).
Cortes, J.E. et al., FT-2102, an IDH1m Inhibitor, Combined with Azacitidine in Patients with Acute Myeloid Leukemia (AML) or Myelodysplastic Syndrome (MDS): Results from a Phase 1 Study, Congress of EHA 2019 Abstract Submission, 4. Acute myeloid leukemia—Clinical, EHA-3328, 2 pages (submitted Mar. 1, 2019).
Cortes, J.E. et al., FT-2102, an IDH1m Inhibitor, Combined with Azacitidine in Patients with Acute Myeloid Leukemia (AML) or Myelodysplastic Syndrome (MDS): Results from a Phase 1 Study, Poster EHA-3328, Presented at the 24th Annual Congress of the European Hematology Association, Amsterdam, Netherlands, Jun. 14, 2019.
Cortes, J.E. et al., FT-2102, an IDH1m Inhibitor, in Combination with Azacitidine in Patients with Acute Myeloid Leukemia (AML) or Myelodysplastic Syndrome (MDS): Results from a Phase 1 Study, ASH abstract available on online meeting program, 9 pages (submitted Jul. 31, 2018, published Nov. 1, 2018).
Cortes, J.E. et al., FT-2102, an IDH1m Inhibitor, in Combination with Azacitidine in Patients with Acute Myeloid Leukemia (AML) or Myelodysplastic Syndrome (MDS): Results from a Phase 1 Study, Poster 1452, Presented at the 60th Annual Meeting of the American Society of Hematology, San Diego, CA (Dec. 1, 2018).
Cortes, J.E. et al., Olutasidenib (FT-2102) Induces Rapid Remissions in Patients with IDH1-Mutant Myelodysplastic Syndrome: Results of Phase 1/2 Single Agent Treatment and Combination with Azacitidine, ASH Annual Meeting, Oral and Poster Abstract, Abstract 674 | (Dec. 9, 2019).
Cortes, J.E. et al., Olutasidenib (FT-2102) Induces Rapid Remissions in Patients with IDH1-Mutant Myelodysplastic Syndrome: Results of Phase 1/2 Single Agent Treatment and Combination with Azacitidine, ASH Annual Meeting, Oral Presentation, 12 pages (Dec. 9, 2019).
Cui, Z. et al., Structure and properties of N-heterocycle-containing benzotriazoles as UV absorbers, Journal of Molecular Structure, 1054: 94-99 (2013).
Cytosar-U, Sterile Cytarabine, USP; Drug Description, Pharmacia & Upjohn Company, Revised Sep. 1997,6 pages (Approved Oct. 15, 1998).
Dai, D. et al., Clinical pharmacokinetics/pharmacodynamics (PK/PD) of ivosidenib in patients with IDH1-mutant advanced hematologic malignancies from a phase 1 study, 2018 ASCO Annual Meeting, J Clin Oneal., 36 (Abstract 2581), 1 page (Jun. 4, 2018). URL: https://meetinglibrary.asco.org/record/158639/abstract [Retrieved Jun. 7, 2018].
Damato, S. et al., IDH1 mutations are not found in cartilaginous tumours other than central and periosteal chondrosarcomas and enchondromas, Histopathology, 60: 357-376 (2011).
Dang, L. et al., Cancer-associated IDH1 mutations produce 2-hydroxyglutarate, Nature, 462: 739-744 (2009).
Dang, L. et al., IDH mutations in cancer and progress toward development of targeted therapeutics, Annals of Oncology, 27: 599-608 (2016).
Dang, L. et al., IDH mutations in glioma and acute myeloid leukemia, Trends Mol. Med., 16(9): 387-397 (2010).
Database Caplus (Online) Chemical Abstracts Service, Columbus, Ohio, US; retrieved from STN Database accession No. 1987:407040 abstract, Prostakov, N.S. et al., Synthesis of substituted 2-pyridones and 4-aza-3-fluorenones, Khimiya Geterotsiklicheskikh Soedinenii, 7: 939-942 (1986).
Database Registry (Online) Chemical Abstracts Service, Columbus, Ohio, US; Database accession No. 1434379-53-9 (Jun. 5, 2013).
Database Registry (Online) Chemical Abstracts Service, Columbus, Ohio, US; Database accession No. 1497653-96-9 (Dec. 18, 2013).
Database Registry (Online) Chemical Abstracts Service, Columbus, Ohio, US; Database accession No. 1567357-55-4 (Mar. 12, 2014).
Database Registry (Online) Chemical Abstracts Service, Columbus, Ohio, US; Database accession No. 1567456-94-3 (Mar. 12, 2014).
De Botton, S. et al., Clinical Safety and Activity of AG-120, a First-in-Class, Potent Inhibitor of the IDH1-Mutant Protein, in a Phase 1 Study of Patients with Advanced IDH-Mutant Hematologic Malignancies. European Hematology Association Learning Center, P563 (2015).
De Botton, S. et al., FT-2102, An IDH1m Inhibitor, Induces Mutation Clearance In Patients With Acute Myeloid Leukemia (AML) Or Myelodysplastic Syndrome (MDS) Treated In Phase 1 Dose Escalation And Expansion Study, Abstract Submission, 4. Acute myeloid leukemia—Clinical, EHA-3251, 2 pages (submitted Mar. 1, 2019).
De Botton, S. et al., FT-2102, an IDH1m Inhibitor, Induces Mutation Clearance in Patients with Acute Myeloid Leukemia (AML) or Myelodysplastic Syndrome (MDS) Treated in Phase 1 Dose Escalation and Expansion Study, Poster EHA-3251, Presented at the 24th Annual Congress of the European Hematology Association, Amsterdam, Netherlands, Jun. 15, 2019.
De La Fuente, M. et al., A Phase 1b/2 Study of Olutasidenib in Patients with Relapsed/Regractory IDH1 Mutant Gliomas: Safety and Clinical Activity as a Single Agent and in Combination with Azacitidine, ASCO, slides 1-13, May 2020.

(56) References Cited

OTHER PUBLICATIONS

De La Fuente, M.I. et al., A phase ib/11 study of olutasidenib in patentis with relapsed/refractory IDH1 mutant gliomas: Safety and efficacy as single agent and in combination with azacitidine, Amer. Soc. Clin. Oneal. (2020), Abstract, <https://meetinglibrary.asco.org/record/185065/abstract>. Retrieved on May 13, 2020.

De La Fuente, M.I. et al., Phase 1b/2 Study of Olutasidenib (FT-2102), an Inhibitor of Mutant IDH1, in Patients with Relapsed/Refractory IDH1-Mutant Gliomas: Preliminary Safety and Clinical Activity, Presented at the Society for NeuroOncology, Phoenix, AZ, Nov. 20-24, 2019 (Presented on Nov. 21, 2019).

DelMar Pharmaceuticals, Inc., DelMar Pharmaceuticals Announces Fast Track Designation for VAL-083 in Recurrent Glioblastoma, 5 pages (Dec. 26, 2017).

Deng, G. et al., Selective Inhibition of Mutant Isocitrate Dehydrogenase 1 (IDH1) via Disruption of a Metal Binding Network by an Allosteric Small Molecule, The Journal of Biological Chemistry, 290: 762-774 (2014).

Derissen, E.J.B. et al., ConciseDrug Review:Azacitidine and-Decitabine, The Oncologist; 18: 619-624 (2013).

Diao, L. and Meibohm, B., Pharmacometric Applications and Challenges in the Development of Therapeutic Antibodies in Immuno-Oncology, Current Pharmacology Reports, 4: 285-291 (2018).

Dinardo, C., Highlights in Acute Myeloid Leukemia From the 2017 American Society of Hematology Annual Meeting and Exposition, Clinical Advance in Hematology & Oncology, 16(3): Suppl 8 (Mar. 2018), A Review of Selected Presentations From the 2017 American Society of Hematology Annual Meeting and Exposition, Atlanta, Georgia, 24 pages (Mar. 8, 2018).

Dinardo, C.D. and Cortes, J.E., Mutations in AML: prognostic and therapeutic implications, Hematology, 348-355 (2016).

Dinardo, C.D. et al., Characteristics, clinical outcome, and prognostic significance of IDH mutations in AML, Am J Hematol., 90(8): 732-736 (2015).

Dinardo, C.D. et al., Durable Remissions with Ivosidenib in IDH1-Mutated Relapsed or Refractory Aml, N Engl J Med, 378: 2386-2398 (2018).

Dinardo, C.D. et al., Ivosidenib (AG-120) in Mutant IDH1 AML and Advanced Hematologic Malignancies: Results of a Phase 1 Dose Escalation and Expansion Study. Presented at: ASH Annual Meeting and Exposition, Atlanta, Georgia. Abstract 725, 3 pages (Dec. 13, 2017).

Dinardo, C.D. et al., Ivosidenib (AG-120) Induced Durable Remissions and Transfusion Independence in Patients with IDH1-Mutant Relapsed or Refractory Myelodysplastic Syndrome: Results from a Phase 1 Dose Escalation and Expansion Study, 2018 ASH Annual Meeting, Blood, 132: Abstract 1812 (2018).

Dinardo, C.D. et al., Ivosidenib (AG-120) Induced Durable Remissions and Transfusion Independence in Patients with IDH1-Mutant Relapsed or Refractory Myelodysplastic Syndrome: Results from a Phase 1 Dose Escalation and Expansion Study, 2018 ASH Annual Meeting, Poster, 132: Abstract 1812 (2018).

Dinardo, C.D. et al., Mutant IDH (miDH) inhibitors, ivosidenib or enasidenib, with azacitidine (AZA) in patients with acute myeloid leukemia (AML), 2018 ASCO Annual Meeting, J Clin Oneal., 36 (Abstract 7042), 2 pages (Jun. 4, 2018). URL: https://meetinglibrary.asco.org/record/162432/abstract [Retrieved Jun. 7, 2018].

Dinardo, C.D. et al., Mutant IDH (MIDH) Inhibitors, Ivosidenib Or Enasidenib, With Azacitidine (AZA) In Patients With Acute Myeloid Leukemia (AML), European Hematology Association, Abstract S1562, 2(S1): 719 (2018).

Dinardo, C.D. et al., Mutant Isocitrate Dehydrogenase (miDH) Inhibitors, Enasidenib or Ivosidenib, in Combination with Azacitidine (AZA): Preliminary Results of a Phase 1b/2 Study in Patients with Newly Diagnosed Acute Myeloid Leukemia (AML), ASH Annual Meeting, Blood, 130: Abstract 639 (2017).

Dinardo, C.D. et al., Mutant Isocitrate Dehydrogenase (miDH) Inhibitors, Enasidenib or Ivosidenib, in Combination with Azacitidine (AZA): Preliminary Results of a Phase 1b/2 Study in Patients with Newly Diagnosed Acute Myeloid Leukemia (AML), Presentation, ASH Annual Meeting, Abstract 639: 14 pages (2017).

Dinardo, C.D. et al., Serum 2-hydroxyglutarate levels predict isocitrate dehydrogenase mutations and clinical outcome in acute myeloid leukemia, Blood, 121(24): 4917-1924 (2013).

Dohner, H., Diagnosis and management of AML in adults: 2017 ELN recommendations from an international expert panel, Blood, 129:424-447 (2017).

Eckmann, K.R. et al., Chemotherapy Outcomes for the Treatment of Unresectable Intrahepatic and Hilar Cholangiocarcinoma: A Retrospective Analysis, Gastrointest Cancer Res 4: 155-160 (2011).

El-Khoueiry, A.B. et al., Nivolumab in patients with advanced hepatocellular carcinoma (CheckMate 040): results of phase 1/2 dose escalation and expansion, USC Norris Comprehensive Cancer Center, 36 paqes (2017).

Emadi, A. et al., Presence of isocitrate dehydrogenase mutations may predict clinical response to hypomethylating agents in patients with acute myeloid leukemia, Am. J. Hematol., 90: E77-E79, (2015).

Estekizadeh, A. et al., Increased cytomegalovirus replication by 5-Azacytidine and viral-induced cytoplasmic expression of DNMT-1 in medulloblastoma and endothelial cells, International Journal of Oncology, 52: 1317-1327 (2018).

Estey E., Acute myeloid leukemia and myelodysplastic syndromes in older patients, JCO, 25: 1908-1915 (2007).

Faderl, S. et al., Clofarabine plus cytarabine compared with cytarabine alone in older patients with relapsed or refractory acute myelogenous leukemia: results from the Classic I trial, J Clin Oneal., 30: 2492-2499 (2012).

Fan, B. et al., Evaluation of the pharmacokinetic/pharmocodynamic (PK/PD) relationships of an oral, selective, first-in-class, potent IDH1 inhibitor, AG-221, from a phase 1 trial in patients with advanced IDH2 mutant positive hematologic malignancies, Blood, 124: 3737, 6 pages (2014). URL: http://www.bloodjournal.org/content/124/21/3737?sso-checked=true [Retrieved May 13, 2019].

Fan, B. et al., Evaluation of the pharmacokinetic/pharmocodynamic (PK/PD) relationships of an oral, selective, first-in-class, potent IDH1 inhibitor, AG-221, from a phase 1 trial in patients with advanced IDH2 mutant positive hematologic malignancies, Poster 3737, Presented at the 56th American Society of Hematology Annual Meeting and Exposition, San Francisco, CA, 1 page(Dec. 8, 2014).

Fan, B. et al., Longitudinal Pharmacokinetic/Pharmacodynamic Profile of AG-120, a Potent Inhibitor of the IDH1 Mutant Protein, in a Phase 1 Study of IDH1-Mutant Advanced Hematologic Malignancies, American Society of Hematology, 57th Annual Meeting & Exposition, Orlando, FL, Abstract 1310, 2 pages (Dec. 508, 2015). URL: https://ash.confex.com/ash/2015/webprogramscheduler/Paper82908.html [Retrieved Jun. 7, 2018].

Fan, B. et al., Longitudinal Pharmacokinetic/Pharmacodynamic Profile of AG-120, a Potent Inhibitor of the IDH1 Mutant Protein, in a Phase 1 Study of IDH1-Mutant Advanced Hematologic Malignancies, Blood, 126(23): 1310-1310 (2015).

Fan, B. et al., Longitudinal pharmacokinetic/pharmacodynamic profile of AG-120, a potent inhibitor of the IDH1 mutant protein, in a phase 1 study of IDH1-mutant advanced hematologic malignancies, Poster 1310, Presented at the 57th American Society of Hematology Annual Meeting and Exposition, Orlando, FL, 1 page (Dec. 5, 2015).

Fan, B. et al., Pharmacokinetic/pharmacodynamic (PK/PD) profile of AG-120 in patients with IDH1-mutant cholangiocarcinoma from a phase 1 study of advanced solid tumors, Poster 4082, Presented at the American Society of Clinical Oncology (ASCO) Annual Meeting, Chicago, IL, USA, 1 page (Jun. 3, 2017).

Fan, B. et al., Pharmacokinetic/Pharmacodynamic (PK/PD) Profile of AG-120 in Patients with IDH1-Mutant Cholangiocarcinoma from a Phase 1 Study of Advanced Solid Tumorsm, Journal of Clinical Oncology, 35(15 suppl): 4082-4082 (May 20, 2017).

Fan, B. et al., Pharmacokinetic/pharmacodynamic evaluation of AG-120, a potent inhibitor of the IDH1 mutant protein, in a phase 1 study of IDH1-mutant advanced hematologic malignancies, Poster P572, Presented at the 20th Congress of the European Hematology Association, Vienna, Austria, 1 page (Jun. 13, 2015).

(56) References Cited

OTHER PUBLICATIONS

Fan, B. et al., Pharmacokinetics/pharmacodynamics (PKIPD) of ivosidenib in patients with IDH1-mutant advanced solid tumors from a phase 1 study, 2018 ASCO Annual Meeting, J Clin Oneal., 36 (Abstract 2577), 1 page (Jun. 4, 2018). URL: https://meetinglibrary.asco.org/record/158587/abstract [Retrieved Jun. 7, 2018].

Fatima, S., Molecular docking and 3D-QSAR studies on inhibitors of DNA damage signaling enzyme human PARP-1, J Receptors and Signal Transduction, 32(4) 214-224 (2012).

Fernandez, H.F. et al., Anthracycline dose intensification in acute myeloid leukemia, NEJM, 361: 1249-1259 (2009).

Figueroa, M.E. et al., Leukemic IDH1 and IDH2 mutations result in a hypermethylation phenotype, disrupt TET2 function, and impair hematopoietic differentiation, Cancer Cell, 18:553-567 (2010).

Flavahan, W.A. et al., Insulator dysfunction and oncogene activation in IDH mutant gliomas, Nature, 1-16 (2015).

FORMA Therapeutics, Best-in-Class miDH1 Inhibitor FT-2102, Presented at JP Morgan 36th Annual Healthcare Conference, San Francisco, California, 24 slides (Jan. 8-11, 2018).

FORMA Therapeutics, Discovery and Optimization of a Novel Series of Inhibitors of mt-IDH1, 7th Annual Advances in Chemical Sciences Symposium, Presentation, 21 slides (May 4, 2018).

FORMA Therapeutics, FORMA Therapeutics and the University of Oxford Announce Multi-Year Collaboration to Advance the Development of Deubiquitinating Enzyme (DUB) Inhibitors for the Treatment of Neurodegenerative Diseases, Press Release, 2 pages (May 9, 2018).

FORMA Therapeutics, FORMA Therapeutics Announces Presentation At The 2018 American Society Of Clinical Oncology (ASCO) Annual Meeting, FT-2102 IDH1m Inhibitor Clinical Data Selected for Oral Presentation, Abstract 7009: 1 page (May 10, 2018).

Frankel, S.R. et al., The "retinoic acid syndrome" in acute promyelocytic leukemia, Ann Intern Med., 117(4): 292-296 (1992).

Gaal, J. et al., Isocitrate Dehydrogenase Mutations Are Rare in Pheochromocytomas and Paragangliomas, J. Clin. Endocrinol. Metab., 95(3): 1274-1278 (2010).

Gainer, J.L. et al., Trans sodium crocetinate with temozolomide and radiation therapy for I glioblastoma multiforme, J. Neurosurg, 126:460-466 (2017).

Ghazanchyan, T. et al., Developing a Genomics Model to Predict Failure of Isocitrate Dehydrogenase (IDH) Inhibitors for Treatment of Patients with IDH1- or IDH2-Mutated Acute Myeloid Leukemia, 2018 ASH Annual Meeting, Blood, 132: Abstract 2815 (2018).

Ghiam, A.F. et al., IDH mutation status in prostate cancer, Oncogene, 31: 3826 (2012).

Golub, D. et al., Mutant Isocitrate Dehydrogenase Inhibitors as Targeted Cancer Therapeutics, Front. Oneal., Article 417, 1-25 (2019).

Gormley, G., Research and Development at Daichii Sankyo, Daiichi-Sankyo, 70 pages | (2014). URL: https://www.daiichisankyo.com/files/news/ir/pdf/005258/R&D%20Day_ eng.pdf.

Goyal, L. et al., Prognosis and Clinicopathologic Features of Patients With Advanced Stage Isacitrate Dehydrogenase (IDH)Mutant and IDHWild-Type Intrahepatic Cholangiocarcinoma, The Oncologist, 20: 1019-1027 (2015).

Gross, S. et al., Cancer-associated metabolite 2-hydroxyglutarate accumulates in acute myelogenous leukemia with isocitrate dehydrogenase 1 and 2 mutations, J. Exp. Med., 207(2): 339-344 (2010).

Gruslove, A. et al., VB-111: a novel anti-vascular therapeutic for glioblastoma multiforme, J Neurooncol., 124(3):365-372 (2015).

Gu, X. et al., MicroRNA-129-5p inhibits human glioma cell proliferation and induces cell cycle arrest by directly targeting DNMT3A, Am. J. Transl. Res., 10(9):2834-2847 (2018).

Hayden, J.T. et al., Frequent IDH1 mutations in supratentorial primitive neuroectodermal tumors (sPNET) of adults but not children, Cell Cycle, 8(11): 1806-1807 (2009).

He, Y. et al., Asperspiropene A, a novel fungal metabolite as an inhibitor of cancer-associated mutant isocitrate dehydrogenase 1, Org. Chem. Front., 1-8 (2017).

Hindson, B.J. et al., High-Throughput Droplet Digital PCR System for Absolute Quantitation of DNA Copy Number, Anal. Chem., 83(22): 8604-8610 (2011).

Hondeghem, L.M. et al., Blinded Test in Isolated Female Rabbit Heart Reliably Identifies Action Potential Duration Prolongation and Proarrhythmic Drugs: Importance of Triangulation, Reverse Use Dependence, and Instability, Journal of Cardiovascular Pharmacology, 41: 14-24 | (2003).

Hondeghem, L.M. et al., Instability and Triangulation of the Action Potential Predict Serious Proarrhythmia, but Action Potential Duration Prolongation Is Antiarrhythmic, Circulation, 103: 2004-2013 (2001).

Huang, J. et al., Isocitrate Dehydrogenase Mutations in Glioma: From Basic Discovery to Therapeutics Development, Front. Oneal., Article 506, 9:1-7 (2019).

ICH Harmonised Tripartite Guideline, Good Manufacturing Practice Guide for Active Pharmaceutical Ingredients Q7, Current Step 4 version, 49 pages (Nov. 10, 2000).

International Search Report for PCT/US2015/051044, 4 pages (mailed Nov. 23, 2015).

International Search Report for PCT/US2015/051046, 3 pages (mailed Oct. 30, 2015).

International Search Report for PCT/US2015/051053, 4 pages (mailed Oct. 28, 2015).

International Search Report for PCT/US2015/051055, 3 pages (mailed Nov. 13, 2015).

International Search Report for PCT/US2015/051056, 4 pages (mailed Nov. 20, 2015).

International Search Report for PCT/US2015/051059, 3 pages (mailed Oct. 30, 2015).

International Search Report for PCT/US2019/032742, 4 pages (mailed Jul. 29, 2019).

International Search Report for PCT/US2019/032747, 5 pages (mailed Aug. 1, 2019).

International Search Report for PCT/US2020/033212, 6 pages (mailed Jul. 20, 2020).

Ishii, Y. et al., Abstract A071: AG-120 (ivosidenib), a first-in-class mutant IDH1 inhibitor, promotes morphologic changes and upregulates liver-specific genes in IDH1 mutant cholangiocarcinoma, Cellular Responses to Therapy, AACR-NCI-EORTC International Conference on Molecular Targets and Cancer Therapeutics, Oct. 26-30, 2017, Philadelphia, PA, 3 pages (Published Jan. 2018).

Janin, M. et al., Serum 2-Hydroxyglutarate Production in IDH1- and IDH2-Mutated De Novo Acute Myeloid Leukemia: A Study by the Acute Leukemia French Association Group, Journal of Clinical Oncology, 32(4): 297-305 (2014).

Jiang, K. et al., Primary Liver Cancers, Part 2: Progression Pathways and Carcinogenesis, Cancer Control, 25(1): 1-9 (2018).

Jones, R.L. et al., A phase ib/11 study of olutasidenib in patients with relapsed/refractory IDH1 mutant solid tumors: Safety and efficacy as single agent, Amer. Soc. Clin. Oneal. (2020), Abstract, <https://meetinglibrary.asco.org/record/186633/abstract>. Retrieved on May 13, 2020.

Jones, S.; et al., Discovery and Optimization of Allosteric Inhibitors of Mutant Isocitrate Dehydrogenase 1 (R132H IDH1) Displaying Activity in Human Acute Myeloid Leukemia Cells, J. Med. Chem., 59(24): 11120-11137 (2016).

Kang, M.R. et al., Mutational analysis of IDH1 codon 132 in glioblastomas and other common cancers, Int. J. Cancer, 125: 353-355 (2009).

Kats, L.M., et al., Proto-oncogenic role of mutant IDH2 in leukemia initiation and maintenance, Cell Stem Cell, 14:329-341 (2014).

Katz, A., Novel Alkylating Agent Defies Mechanisms of Resistance in GBM Tumors, Oncologylive, 18(19): (Oct. 11, 2017).

Kintara Therapeutics, DelMar Presents Clinical Update on VAL-083 From Ongoing First- and Second-Line Trials in Patients with MGMT-unmethylated GBM at The Society for NeuroOncology Annual Meeting, 5 pages (Nov. 20, 2018). URL: https://www.kintara.com/news-media/press-releases/detail/887/delmar-presents-clinical- update-on-val-083-from-ongoing.

Koivunen, P. et al., Transformation by the R Enantiomer of 2-Hydroxyglutarate Linked to EgiN Activation, Nature, 483(7390): 484-488 (2013).

(56) References Cited

OTHER PUBLICATIONS

Kombarov, R.V. et al., CA Accession No. 138:368869, abstract only of Chem of Het Compounds, 38(9): 1154-1155 (2002).

Kopinja, J. et al., A Brain Penetrant Mutant IDH1 Inhibitor Provides In Vivo Survival Benefit, Scientific Reports, 7: 13853, 14 pages (2017).

Kurz, S.C. and Wen, P.Y., Quo Vadis—Do Immunotherapies Have a Role in Glioblastoma?, Curr Treat Options Neural, 20: 14, 1-23 (2018).

Labussiere, M. et al., IDH1 Gene Mutations: A New Paradigm in Glioma Prognosis and Therapy?, The Oncologist, 15: 196-199 (2010).

Law, J. M.; et al., Discovery of 8-Membered Ring Sulfonamides as Inhibitors of Oncogenic Mutant Isocitrate Dehydrogenase 1. ACS Medicinal Chemistry Letters, 7(10): 944-949 (2016).

Le, K. et al., Population Pharmacokinetics of Ivosidenib (AG-120) in Patients with IDH1-Mutant Advanced Hematologic Malignancies, 2018 ASH Annual Meeting, Blood, 132: Abstract 1394 (2018).

Le, K. et al., Population Pharmacokinetics of Ivosidenib (AG-120) in Patients with IDH1-Mutant Advanced Hematologic Malignancies, Poster, 2018 ASH Annual Meeting, 132: Abstract 1394 (2018).

Lee, J.H. et al., IDH1 R132C mutation is detected in clear cell hepatocellular carcinoma by | pyrosequencing, World Journal of Surgical Oncology, 15: 82, 8 pages (2017).

Leese, C. L. and Rydon, H.N., Polyazanaphthalenes. Part I. Some derivatives of 1:4:5-triazanaphthalene and quinoxaline, PolyJournal of the Chemical Society, 303-309 (1995).

Levell, J. R. et al., Optimization of 3-pyrimidin-4-yl-oxazolidin-2-ones as allosteric and mutant specific inhibitors of IDH1, ACS Med. Chem. Lett., 8:151-156 (2017).

Lin, J. et al., Discovery and Optimization of Quinolinone Derivatives as Potent, Selective, and Orally Bioavailable Mutant Isocitrate Dehydrogenase 1 (miDH1) Inhibitors, J. Med. Chem., 62(14):6575-6596 (2019).

Liu, G. et al., Catalytic Asymmetric Synthesis of tert-Butanesulfinamide. Application to the Asymmetric Synthesis of Amines, J. Am. Chem. Soc., 119: 9913-9914 (1997).

Liu, G. et al., Synthesis of enantiomerically pure N-tert-butanesulfinyl imines (tertbutanesulfinimines) by the direct condensation of tert-butanesulfinamide with aldehydes and ketones. J. Org. Chem., 64(6): 1278-1284 (1999).

Liu, Z. et al., Inhibition of cancerassociated mutant isocitrate dehydrogenases: synthesis, structureactivity relationship, and selective antitumor activity. J. Med. Chem., 57: 8307-8318 1(2014).

Lopez, G.Y. et al., IDH1 mutation identified in human melanoma, Biochem Biophys Res Commun., 398(3): 585-587 (2010).

Losman, J-A. et al., (R)-2-Hydroxyglutarate is Sufficient to Promote Leukemogenesis and its Effects are Reversible, Science, 339(6127): 9 pages (2013).

Lowery, M.A. et al., A phase 3, multicenter, randomized, double-blind study of AG-120 vs placebo in patients with an advanced cholangiocarcinoma with an IDH1 mutation, ASCO Annual Meeting 2017, J Clin Oneal, 35: suppl; Abstract TPS4142 (2017).

Lowery, M.A et al., Phase I study of AG-120, an IDH1 mutant enzyme inhibitor: Results from the cholangiocarcinoma dose escalation and expansion cohorts, Abstract 4015, Journal of Clinical Oncology, 35 (15 Suppl): 4015-4015 (May 20, 2017). URL: http://ascopubs.org/doilabs/10.1200/JC0.2017.35.15 suppl.4015 [Retrieved Mar. 21, 2018].

Lu, C. et al., IDH mutation impairs histone demethylation and results in a block to cell differentiation, Nature, 483(7390): 474-478 (2012).

Lu, C. et al., Induction of sarcomas by mutant IDH2, Genes & Development, 27: 1986-1998 (2013).

Ma, R. and Yun, C. H., Crystal structures of pan-IDH inhibitor AG-881 in complex with mutant human IDH1 and IDH2, Biochem Biophys Res Commun, 503(4): 2912-2917 (2018).

Mahmood, 1., Prediction of Clearance, Volume of Distribution and Half-life by Allometric Scaling and by use of Plasma Concentrations Predicted from Pharmacokinetic Constants: a Comparative Study, J. Pharm. Pharmacal., 51: 905-910 (1999).

Mamedov, V. A. et al., Synthesis and Functionalization of 3-Ethylquinoxalin-2(1H)-one, Russian Journal of Organic Chemistry, 41(4): 599-606 (2005).

Mantica, M. et al., Retrospective study of nivolumab for patients with recurrent high grade | gliomas, Journal of Neuro-Oncology, 139: 625-631 (2018).

Mardis, E.R. et al., Recurring Mutations Found by Sequencing an Acute Myeloid Leukemia Genome, N Engl J Med, 361(11): 1058-1066 (2009).

Mcbrayer, S.K. et al., Transaminase Inhibition by 2-Hydroxyglutarate Impairs Glutamate Biosynthesis and Redox Homeostasis in Glioma, Cell, 175: 101-116 (2018).

Medeiros, B.C. et al., Isocitrate dehydrogenase mutations in myeloid malignancies, Leukemia, 31: 272-281 (2017).

Meg[as-Vericat, J.E., et al., IDHI-mutated relapsed or refractory AML: current challenges and future prospects, Blood and Lymphatic Cancer: Targets and Therapy, 9:19-32 (2019).

Meijer, D. et al., Genetic Characterization of Mesenchymal, Clear Cell, and Dedifferentiated Chondrosarcoma, Genes, Chromosomes & Cancer, 51:899-909 (2012).

Mellai, M., et al., The Distribution and Significance of IDH Mutations in Gliomas, Evolution of the Molecular Biology of Brain Tumors and the Therapeutic Implications, Terry Lichtor, IntechOpen, DOI: 10.5772/52357, 23 paqes (2013).

Mellinghoff, I. et al., AG-120, A First-in-Class Mutant IDH1 Inhibitor in Patients with Recurrent or Progressive IDH1 Mutant Glioma: Updated Results from the Phase 1 Non-Enhancing Glioma Population, Presentation ACTR-46, Society for Neuro-Oncology Annual Scientific Meetinq, Nov. 16-19, 2017, San Francisco, CA, USA (2017).

Mellinghoff, I. et al., Phase 1 study of AG-881, an inhibitor of mutant IDH1 and IDH2: results from the recurrent/progressive glioma population, Presentation ACTR-31, 23rd Annual Scientific Meeting and Education Day of the Society for Neuro-oncology (SNO), Nov. 15-18, 2018, New Orleans, LA, USA (2018).

Mellinghoff, I.K. et al., A phase 1, multicenter, randomized, open-label, perioperative study of AG-120 (ivosidenib) and AG-881 in patients with recurrent, nonenhancing, IDH1-mutant, low-grade glioma, Presented at the 23rd Annual Scientific Meeting and Education Day of the Society for Neuro-oncology (SNO), New Orleans, LA, USA, Poster RBTT-03 (Nov. 15-18, 2018).

Mellinghoff, I.K. et al., A phase 1, open-label perioperative study of ivosidenib (AG-120) and vorasidenib (AG-881) in recurrent, IDH1-mutant, low-grade glioma: Results from Cohort 1, Presented at the American Society of Clinical Oncology (ASCO) Annual Meeting, May 21-Jun. 3, 2019, Chicago, IL, USA.

Mellinghoff, I.K. et al., AG-120, a first-in-class mutant IDH1 inhibitor in patients with recurrent or progressive IDH1 mutant qlioma: results from the phase 1 qlioma expansion cohorts, Presented at the Society for Neuro-Oncology Annual Scientific Meeting, Scottsdale, AZ, ACTR-46: 19 pages (Nov. 18, 2016).

Mellinghoff, I.K. et al., Phase 1 study of AG-881, an inhibitor of mutant IDH1/IDH2, in patients with advanced IDH-mutant solid tumors, including glioma, 2018 ASCO Annual Meeting, J Clin Oncol., 36: (Abstract 2002), 2 pages (Jun. 1, 2018). URL: https://meetinglibrary.asco.org/record/162680/abstract [Retrieved Jun. 7, 2018].

Metallo, C.M. et al., Reductive glutamine metabolism by IDH1 mediates lipogenesis under hypoxia, Nature, 481(7381):380-384 (2011).

Meth-Cohn, O. and Stanforth, S. P. The Vilsmeier-Haack reaction (Review), Compr. Org. Synth., 2: 777-779 (1991).

Metzker, M., Sequencing technologies—the next generation, Nature Review Genetics, 11:31-46 (2010).

Mohamed, E.A. et al., CA Accession No. 122:160601, abstract only of Indian J Chern, Sect B: Org Chern Inc Med Chern, 34B(1): 21-26 (1995).

Mohamed, H. and Duffy-Warren, F., FT-2102-miDH1 Inhibitor, Forma Therapeutics presentation, 4th Paediatric Strategy Forum for

(56) References Cited

OTHER PUBLICATIONS

Medicinal Product Development for Acute Myeloid Leukaemia in Children and Adolescents, Erasmus University Rotterdam, 7 pages (Apr. 11, 2019).
Molenaar, R.J. et al., Wild-type and mutated IDH1/2 enzymes and therapy responses, Oncogene, 37: 1949-1960 (2018).
Morshed, M.N. et al., Computational approach to the identification of novel Aurora-A inhibitors, Bioorg & Med Chern, 19:907-916 (2011).
National Comprehensive Cancer Network, Inc., NCCN Clinical Practice Guidelines in Oncology (NCCN Guidelines®), Acute Myeloid Leukemia, Version 2.2018 (Aug. 1, 2018).
Nicolay, B. et al., Combined use of the pan-IDH mutant inhibitor AG-881 with radiation therapy shows added benefit in an orthotopic IDH1 mutant glioma model in vivo, Poster EXTH-34, Presented at the 22nd Annual Scientific Meeting and Education Day of the Society for Neuro-oncology, Nov. 16-19, 2017, San Francisco, CA, USA (2017).
Nicolay, B. et al., The IDH1 mutant inhibitor AG-120 shows strong inhibition of 2-HG production in an orthotopic IDH1 mutant glioma model in vivo, EXTH-59, Presented at the 22nd Annual Scientific Meeting and Education Day of the Society for Neuro-oncology, Nov. 16-19, 2017, San Francisco, CA, USA (2017).
Okoye-Okafor, U.C. et al., New IDH1 mutant inhibitors for treatment of acute myeloid leukemia, Nat. Chern. Bioi., 11: 878-886 (2015).
Olutasidenib, C18H15CIN4O2, PubChem, Compound Summary, 10 pages (retrieved Jul. 24, 2019).
Oran, B. and Weisdorf, D. Survival for older patients with acute myeloid leukemia: a | population-based study, Haematologica, 97: 1916-1924 (2012).
Panknin, O. et al., Abstract 2645: BAY 1436032: A highly selective, potent and orally available inhibitor of mutant forms of IDH1, AACR 107th Annual Meeting Apr. 16-26, 2016, 4 |pages.
Pansuriya, T.C. et al., Somatic mosaic IDH1 and IDH2 mutations are associated with enchondroma and spindle cell hemangioma in Oilier disease and Maffucci syndrome, Nature Genetics, 43(12): 1256-1261 (2011).
Parsons, D.W. et al., An Integrated Genomic Analysis of Human Glioblastoma Multiforme, Science, 321(5897): 1807, 15 pages (2008).
Paschka, P. et al., IDH1 and IDH2 mutations are frequent genetic alterations in acute myeloid leukemia and confer adverse prognosis in cytogenetically normal acute myeloid leukemia with NPM1 mutation without FLT3 internal tandem duplication, J Clin Oncol., 22:3636-3643 (2010).
Pelosi, E. et al., Isocitrate dehydrogenase mutations in human cancers: physiopathologic mechanisms and therapeutic Targeting. Journal of Exploratory Research in Pharmacology, 1: 20-34 (2016).
Penard-Lacronique, V. and, Bernard, O.A., IDH1, Histone Methylation, and So Forth, Cancer Cell, 30: 192-194 (2016).
Peng, D. et al., Epigenetic silencing of Th1 type chemokines shapes tumor immunity and immunotherapy, Nature, 527(7577): 249-253 (2015).
Pleyer, L., et al., Azacitidine for Front-Line Therapy of Patients with AML: Reproducible Efficacy Established by Direct Comparison of International Phase 3 Trial Data with Registry Data form the Austrian Azacitidine Registry of the AGMT Study Group, J. Mol. Sci., 18(415):1-18 (2017).
Pollyea, D.A. et al., Ivosidenib (AG-120) in Mutant IDH1 Relapsed/Refractory Acute Myeloid Leukemia: Results of a Phase 1 Study, European Hematology Association, Abstract S1560, 2(S1): 718 (2018).
Pollyea, D.A. et al., Ivosidenib (IVO; AG-120) in mutant IDH1 relapsed/refractory acute myeloid leukemia (R/R AML): Results of a phase 1 study, 2018 ASCO Annual Meeting, J Clin Oneal., 36 (Abstract 7000), 2 pages (Jun. 2, 2018). URL: https://meetinglibrary.asco.org/record/161682/abstract [Retrieved Jun. 7, 2018].

Popovici-Muller, J. et al., Discovery of AG-120 (Ivosidenib): A First-in-Class Mutant IDH1 Inhibitor for the Treatment of IDH1 Mutant Cancer, ACS Med. Chem. Lett., 9(4): 300-305 | c2018).
Popovici-Muller, J. et al., Discovery of the First Potent Inhibitors of Mutant IDH1 That Lower Tumor 2-HG in Vivo, ACS Med. Chem. Lett., 3(10): 850-855 (2012).
Prensner, J.R. and Chinnaiyan, A.M., Metabolism unhinged: IDH mutations in cancer, Nature Medicine, 17(3): 291-293 (2011).
Press Release, Forma Therapeutics Announces Clinical Data to be Presented at ASC020 Virtual Scientific Program (2020), Forma Therapeutics, <https://www.formatherapeutics.com/press-releases/forma-therapeutics-announces-clinical- data-to-be-presented-at-asco20-virtual-scientific-proqram>. Retrieved Jun. 5, 2020.
Prostakov, N.S. et al., Chemistry of Heterocyclic Compounds, CHCCAL, 22(7): 685-810 | (1986).
Pusch, S. et al., Pan-mutant IDH1 inhibitor BAY 1436032 for effective treatment of IDH1 mutant astrocytoma in vivo. Acta Neuropathologica, 133(4): 629-644 (2017).
Ravandi, F. et al., Vosaroxin plus cytarabine versus placebo plus cytarabine in patients with first relapsed or refractory acute myeloid leukemia (VALOR): a randomized, controlled, double-blind, multinational, phase 3 study, Lancet Oneal., 16: 1025-1036 (2015).
Reardon, D.A. et al., Efficacy and safety results of ABT-414 in combination with radiation and temozolomide in newly diagnosed glioblastoma, Neuro-Oncology, 19(7):965-975 (2016).
Reitman, Z.J. and Yan, H, Isocitrate Dehydrogenase 1 and 2 Mutations in Cancer: Alterations at a Crossroads of Cellular Metabolism, J. Natl. Cancer Inst., 102:932-941 (2010).
Ribadeneira, M. et al., SCIDOT-42. FT-2102—A Potent and Selective Brain Penetrant Inhibitor of Mutant Isocitrate Dehydrogenase, Neuro-Oncology, 21(Supplement 6): vi280 3 pages (2019).
Ribadeneira, M.D. et al., Olutasidenib (FT-2102) A Potent and Selective Brain Penetrant Inhibitor of Mutant Isocitrate Dehydrogenase 1, Forma Therapeutics, Inc., Presented at 3rd SNO-SCIDOT Joint Conference on Therapeutic Delivery to the CNS, 9 pages (Nov. 20, 2019).
Roboz, G.J. et al., International randomized Phase 21 study of elacytarabine versus investigator choice in patients with relapsed/refractory acute myeloid leukemia, J Clin Oneal., 20: 1919-1926 (2014).
Roboz, G.J. et al., Ivosidenib (AG-120) Induced Durable Remissions and Transfusion Independence in Patients with IDH1-Mutant Untreated AML: Results from a Phase 1 Dose Escalation and Expansion Study, ASH Annual Meeting, Blood, 132: Abstract 561 (2018).
Roboz, G.J. et al., Ivosidenib (AG-120) Induced Durable Remissions and Transfusion Independence in Patients with IDH1-Mutant Untreated AML: Results from a Phase 1 Dose Escalation and Expansion Study, Presentation, Presented at the 60th American Society of Hematology (ASH) Annual Meeting, Dec. 1-4, 2-18, San Diego, CA, USA, 16 pages, Abstract 561 (2018).
Rohle, D. et al., An Inhibitor of Mutant IDH1 Delays Growth and Promotes Differentiation of Glioma Cells, Science, 340(6132): 626-630 (2013). Supplementary Materials, 32 pages.
Rowe, J.M., AML in 2017: Advances in clinical practice, Best Practice & Research Clinical Haematology, 30: 283-286 (2017).
Saha, S.K. et al., IDH mutations in liver cell plasticity and biliary cancer, Cell Cycle, 13(20): 3176-3182 (2014).
Saha, S.K. et al., Mutant IDH inhibits HNF-4a to block hepatocyte differentiation and promote biliary cancer, Nature, 19 pages (2014).
Sasaki, M. et al., D-2-hydroxyglutarate produced by mutant IDH1 perturbs collagen maturation and basement membrane function, Genes & Development, 26: 2038-2049 (2012).
Sasaki, M. et al., IDH1(R132H) mutation increases murine haematopoietic progenitors and alters epigenetics, Nature, 488(7413): 656-659 (2012).
Schnittger, S. et al., IDH1 mutations are detected in 6.6% of 1414 AML patients and are associated with intermediate risk karyotype and unfavorable prognosis in adults younger than 60 years and unmutated NPM1 status, Blood, 116(25): 5486-5496 (2010).
Schrader, F.C. et al., Novel Type II Fatty Acid Biosynthesis (FAS II) Inhibitors as Multistage Antimalarial Agents, Chem Med Chem, 8: 442-461 (2013).

(56) References Cited

OTHER PUBLICATIONS

Segall, M., Multi-parameter Optimisation in Drug Discovery: Quickly targeting compounds with a good balance of properties, Optibrium Ltd, ELRIG Drug Discovery 2011, 32 pages | (Sep. 7, 2011).
Sellner, L. et al. Increased levels of 2-hydroxyglutarate in AML patients with IDH1-R132H and IDH2-R140Q mutations, Eur. J. Haematol., 85: 457-459 (2010).
Seltzer, M.J. et al., Inhibition of Glutaminase Preferentially Slows Growth of Glioma Cells with Mutant IDH1, Cancer Research, 70(22): 8981-8987 (2010).
Shanley, M., Phase 3 Results Reveal Combination Therapy Does Not Improve Overall Survival in Glioblastoma, HCP Live, 2 pages (Mar. 8, 2018). URL: https://www.hcplive.com/view/vb-111-combination-glioblastoma-fail.
Shibata, T. et al., Mutant IDH1 Confers an in Vivo Growth in a Melanoma Cell Line with BRAF Mutation, Am. J. Pathol., 178(3): 1395-1402 (2011).
Skrzypiec-Spring, M. et al., Isolated heart perfusion according to Langendorff—Still viable in the new millennium, Journal of Pharmacological and Toxicological Methods, 55: 113-126 | (2007).
Sri Ramya, P.V. et al., Curcumin inspired 2-chloro/phenoxy quinoline analogues: Synthesis and biological evaluation as potential anticancer agents, Bioorganic & Medicinal Chemistry Letters 28: 892-898 (2018).
Stein, E. et al., AGILE: A phase 3, multicenter, randomized, placebo-controlled study of ivosidenib in combination with azacitidine in adult patients with previously untreated acute myeloid leukemia with an IDH1 mutation, Journal of Clinical Oncology, 36(15 suppl): Abstract TPS7074 (2018).
Stein, E. et al., AGILE: A phase 3, multicenter, randomized, placebo-controlled study of ivosidenib in combination with azacitidine in adult patients with previously untreated acute myeloid leukemia with an IDH1 mutation, Presented at the American Society of Clinical Oncology (ASCO) Annual Meeting, Chicago, IL, USA, Abstract TPS7074, J Clin Oneal 36, 2018 (Jun. 1-5, 2018).
Stein, E.M. et al., Ivosidenib or Enasidenib Combined with Induction and Consolidation Chemotherapy in Patients with Newly Diagnosed AML with an IDH1 or IDH2 Mutation Is Safe, Effective, and Leads to MRD-Negative Complete Remissions, Poster Presented at the 60th American Society of Hematology (ASH) Annual Meeting, Dec. 1-4, 2018, San Diego, CA, USA, 21 pages, Abstract 560 (2018).
Stein, E.M. et al., Ivosidenib or Enasidenib Combined with Standard Induction Chemotherapy Is Well Tolerated and Active in Patients with Newly Diagnosed AML with an IDH1 or IDH2 Mutation: Initial Results from a Phase 1 Trial, 2017 ASH Annual Meeting, Blood, 130: Abstract 726 (2017).
Stein, E.M. et al., Molecular remission and response patterns in patients with mutant-IDH2 acute myeloid leukemia treated with enasidenib, Blood, 133(7): 676-0867 (2019).
Stone, R.M. et al., Genetic Profiling and Deep IDH1 Mutation Clearance to =0.04 in Ivosidenib (AG-120)-Treated Patients with Mutant IDH1 Relapsed or Refractory and Untreated AML, 2017 ASH Annual Meeting, Blood, 130: Abstract 2684 (2017).
Struys, E.A. et al., Investigations by mass isotopomer analysis of the formation of D-2-hydroxyglutarate by cultures lymphoblasts from two patients with D-2-hydroxyglytaric aciduria, FEBS Letters, 557: 115-120 (2004).
Struys, E.A. et al., Mutations in the D-2-Hydroxyglutarate Dehydrogenase Gene Cause D-2-Hydroxyglutaric Aciduria, Am. J. Hum. Genet., 76:358-360 (2005).
Study to evaluate FT-2012 as a single agent or in combination with Azacitidine or Cytarabine in patients with Acute Myeloid Leukemia or Myelodysplastic Syndrome, Spanish Clinical Studies Registry, retrieved from https://reec.aemps.es/reec/public/detail.html, 14 pages (2018).
Suman, P. et al., Synthesis and evaluation of functionalized aminobenzoboroxoles as potential anti-cancer agents, Journal of Organometallic Chemistry, 798(1): 125-131 (2015).

Szopa, W. et al., Diagnostic and Therapeutic Biomarkers in Glioblastoma: Current Status and Future Perspectives, BioMed Res. Inter., 1-14 (2017).
Talati, C. and Sweet, K., Recently approved therapies in acute myeloid leukemia: A complex treatment landscape, Leukemia Research, 73: 58-66 (2018).
The Brain Tumour Charity, Positive results from a drug treating recurrent glioblastoma, (Jun. 28, 2018) URL: https://news.abbvie.com/news/abbvie-receives-US-fda-rare-pediatric-disease-designation-for-investigational-abt-414-for-treatment-type-pediatric-brain-tumor-known-as-diffuse-intrinsic-pontine-glioma-dipg.htm.
Thompson, C.B., Metabolic Enxymes as Oncogenes or Tumor Suppressors, N Engl J Med, 360(8): 813-815 (2009).
Thomson, B. and Lipford, K., A Phase 1b/2 Study of FT-2102 in Patients with Advanced Solid Tumors and Gliomas with an IDH1 Mutation, Poster Presented at the Cholangiocarcinoma Foundation Annual Conference, Salt Lake City, UT (Jan. 30, 2019).
Tibsovo Prescription Label, 20 pages (issued Jul. 20, 2018). URL:<https://www.accessdata.fda.gov/druqsatfda docs/label/2018/211192s0001bl.pdf>.
Tintori, C. et al., Identification of Hck Inhibitors As Hits for the Development of Antileukemia and Anti-HIV Agents, Chem Med Chem, 8: 1353-1360 (2013).
Turcan, S. et al., Efficient induction of differentiation and growth inhibition in IDH1 mutant glioma cells by the DNMT Inhibitor Decitabine, Oncotarget, 4(10): 1729-1736 (2013).
U.S. Food and Drug Administration, FDA approves ivosidenib for relapsed or refractory acute myeloid leukemia, 2 pages (Content current as of Jan. 23, 2019). URL: https://www.fda.gov/drugs/resources-information-approved-drugs/fda-approves-ivosidenib-relapsed-or-refractory-acute-myeloid-leukemia.
U.S. Food and Drug Administration, ivosidenib, Treatment of acute myeloid leukemia (AML), 2 pages (Date Designated Jun. 9, 2015). URL: https://www.accessdata.fda.gov/scripts/opdlisting/oopd/detailedIndex.cfm?cfgridkey=481515.
U.S. Food and Drug Administration, ivosidenib, Treatment of cholangiocarcinoma, 1 page (Date Designated Apr. 26, 2017). URL: https://www.accessdata.fda.gov/scripts/opdlisting/oopd/detailedIndex.cfm?cfgridkey=562216.
U.S. Food and Drug Administration, ivosidenib, Treatment of glioma, 1 page (Date Designated May 1, 2018). URL: https://www.accessdata.fda.gov/scripts/opdlisting/oopd/detailedIndex.cfm?cfgridkey=637718.
U.S. Food and Drug Administration, vorasidenib, Treatment of glioma, 1 page (Date Designated Sep. 10, 2018). URL: https://www.accessdata.fda.gov/scripts/opdlisting/oopd/detailedIndex.cfm?cfgridkey=649318.
U.S. Food and Drug Adminsitration, Facts About the Current Good Manufacturing Practices (CGMPs), 1 page (2018), URL: https://www.fda.gov/drugs/pharmaceutical-quality-resources/facts-about-current-qood-manufacturing-practices-cqmps.
Urban, D. J. et al., Assessing inhibitors of mutant isocitrate dehydrogenase using a suite of pre-clinical discovery assays, Scientific Reports 7(1): 12758 (2017).
Valle, J. et al., Cisplatin plus Gemcitabine versus Gemcitabine for Biliary Tract Cancer, N Engl J Med, 362: 1273-1281 (2010).
VBL Therapeutics, Data Demonstrate Strengthened Overall Survival Benefit in Patients Treated With VB-111 in Combination With Bevacizumab, 4 pages (Jun. 1, 2015). URL: vblrx.com/vbl-therapeutics-reports-updated-interim-results-from-phase-2-clinical-trial-of-vb-111-in-recurrentglioblastoma-rgbm/.
VBL Therapeutics, VBL Therapeutics Announces Third Quarter 2018 Financial Results, 6 pages (Nov. 20, 2018). URL: https://www.globenewswire.com/news-release/2018/11/20/1654366/0/enNBL-Therapeutics-Announces-Third-Quarter-2018-Financiai-Results.html.
Venkanna, P. et al., 2,4,6-Trichloro-1,3,5-triazine and N,N'-dimethylformamide as an effective Vilsmeier-Haack reagent for the synthesis of 2-chloro-3-formyl quinolines from acetanilides, Tetrahedron Letters, 56(37): 5164-5167 (2015).
Vidaza, Azacitidine for injection; Drug Description, Manufactured For Pharmion Corporation, Manufactured By Ben Venue Laboratories, Inc., 19 pages (Edition Date: Jan. 9, 2007).

(56) References Cited

OTHER PUBLICATIONS

Vogelstein, B. and Kinzler, K.W., Digital PCR, Proc. Natl. Acad. Sci. USA, 96: 9236-9241 (1999).
Wager, T.T. et al., Defining Desirable Central Nervous System Drug Space through the Alignment of Molecular Properties, in Vitro ADME, and Safety Attributes, ACS Chem. Neurosci., 1:420-434 (2010).
Wager, T.T. et al., Moving beyond Rules: The Development of a Central Nervous System Multiparameter Optimization (CNS MPO) Approach to Enable Alignment of Druglike Properties. ACS Chem. Neurosci., 1(6): 435-449 (2010).
Wahl, D.R. et al., Glioblastoma Therapy Can be Augmented by Targeting IDH1-mediated NADPH Biosynthesis, Cancer Res, 77(4): 960-970 (2017).
Wai, J et al., Synthesis and evaluation of 2-pyridinone derivatives as specific HIV-1 reverse transcriptase inhibitors. 3. Pyridyl and phenyl analogs of 3-aminopyridin-2(1H)-one, J. Med. Chem., 36(2):249-255 (1993).
Wakayama, M. and Ellman, J.A., Recycling the tert-Butanesulfinyl Group in the Synthesis of Amines Using tert-Butanesulfinamide, J. Org. Chem., 74: 2646-2650 (2009).
Wakimoto, H. et al., Targetable Signaling Pathway Mutations Are Associated with Malignant Phenotype in IDH-Mutant Gliomas, Clin Cancer Res, 20(11): 2898-2909 (2014).
Wang, F. et al., Targeted Inhibition of Mutant IDH2 in Leukemia Cells Induces Cellular Differentiation, Science, 340: 622-626 (2013).
Wang, M. et al., Molecular Mutation and Their Cooccurrences in Cytogenetically Normal Acute Myeloid Leukemia, Hindawi Publishing Stem Cells International, 1-11 (2017).
Wang, P. et al., Mutations in Isocitrate Dehydrogenase 1 and 2 Occur Frequently in Intrahepatic Cholangiocarcinomas and Share Hypermetylation Targets with Glioblastomas, Oncogene, 32(25): 3091-3100 (2013).
Wang, R. et al., Rapid Ti(OiPr)4 facilitated synthesis of a,a,a-trisubstituted primary amines by the addition of Grignard reagents to nitriles under microwave heating conditions. Tetrahedron Letters, 50(50): 7070-7073 (2009).
Ward, P.S. et al., The common feature of leukemia-associated IDH1 and IDH2 mutations is a neomorphic enzymatic activity that converts a-ketoglutarate to 2-hydroxyglutarate, Cancer Cell, 17(3): 225-234 (2010).
Ward, P.S. et al., The Potential for Isocitrate Dehydrogenase Mutations to Produce 2-Hydroxyglutarate Depends on Allele Specificity and Subcellular Compartmentalization, The Journal Of Biological Chemistry, 288(6): 3804-3815 (2013).
Watanabe, T. et al., IDH1 Mutations are early events in the Development of Astrocytomas and Oligodendrogliomas, American Journal of Pathology, 174(4): 1149-1153 (2009).
Waters, N.J. et al., Validation of a rapid equilibrium dialysis approach for the measurement of plasma protein binding, J Pharm Sci., 97(10): 4586-4595 (2008).
Watts, J.M. et al., A Phase 1 Dose Escalation Study of the IDH1m Inhibitor, FT-2102, in Patients with Acute Myeloid Leukemia or Myelodysplastic Syndrome, ASCO Abstract public release May 16, 2018, Presented Jun. 4, 2018, Clin Oneal 36, 2018 (suppl; abstr 7009).
Watts, J.M. et al., A Phase 1 Dose Escalation Study of the IDH1m Inhibitor, FT-2102, in Patients with Acute Myeloid Leukemia or Myelodysplastic Syndrome, Presented at the 2018 ASCO Annual Meetings, 19 pages (Jun. 4, 2018).
Watts, J.M. et al., Olutasidenib (FT-2102), an IDH1m Inhibitor As a Single Agent or in Combination with Azacitidine, Induces Deep Clinical Responses with Mutation Clearance in Patients with Acute Myeloid Leukemia Treated in a Phase 1 Dose Escalation and Expansion Study, ASH Annual Meeting, Oral and Poster Abstract, Abstract 231 (Dec. 7, 2019).
Watts, J.M. et al., Olutasidenib (FT-2102), an IDH1m Inhibitor As a Single Agent or in Combination with Azacitidine, Induces Deep Clinical Responses with Mutation Clearance in Patients with Acute Myeloid Leukemia Treated in a Phase 1 Dose Escalation and Expansion Study, ASH Annual Meeting, Oral Presentation, 14 pages (Dec. 7, 2019).
Watts, J.M. et al., Phase 1 Study of the IDH1m Inhibitor FT-2102 as a Single Agent in Patients with IDH1m Acute Myeloid Leukemia (AML) or Myelodysplastic Syndrome (MDS), ASH abstract available in online meeting program, 8 pages (submitted Jul. 31, 2018, published Nov. 1, 2018).
Watts, J.M. et al., Phase 1 Study of the IDH1m Inhibitor FT-2102 as a Single Agent in Patients with IDH1m Acute Myeloid Leukemia (AML) or Myelodysplastic Syndrome (MDS), Poster 1453, Presented at the 60th Annual Meeting of the American Society of Hematology, San Diego, CA (Dec. 1, 2018).
Wheeler, D.A. and Robers, L.R., The Cancer Genome Atlas Research Network, Comprehensive and Integrative Genomic Characterization of Hepatocellular Carcinoma, Cell, 169: 1327-1341 (2017).
Wick, W. et al., New (alternative) temozolomide regimens for the treatment of glioma, Neuro-Oncology, 11:69-79 (2009).
Wu, F. et al., Inhibition of cancer-associated mutant isocitrate dehydrogenases by 2-thiohydantoin compounds, J. Med. Chem., 58: 6899-6908 (2015).
Xu, W. et al., Oncometabolite 2-Hydroxyglutarate Is a Competitive Inhibitor of a-Ketoglutarate-Dependent Dioxygenases, Cancer Cell, 19: 17-30 (2011).
Xu, X. et al., Structures of human cytosolic NADP-dependent isocitrate dehydrogenase reveal a novel self-regulatory mechanism of activity, J Biol Chem., 279(32): 33946-33957 (2004).
Yamashita, A.S. et al., Demethylation and epigenetic modification with 5-azacytidine reduces IDH1 mutant glioma growth in combination with temozolomide, Neuro-Oncology, 21(2): 189-200 (2019).
Yan, H et al., IDH1 and IDH2 Mutations in Gliomas, The New England Journal of Medicine, 360(8):765-773(2009).
Yang, H. et al., IDH1 and IDH2 Mutations in Tumorigenesis: Mechanistic Insights and Clinical Perspectives, Clin Cancer Res, 18(20): 5562-5571 (2012).
Yen, K. et al., Abstract 4956: Functional characterization of the ivosidenib (AG-120) and azacitidine combination in a mutant IDH1 AML cell model, Experimental and Molecular Therapeutics, Proceedings: AACR Annual Meeting 2018; Apr. 14-18, 2018; Chicago, IL | (Published Jul. 2018).
Yen, K. et al., Abstract B126: AG-881, a brain penetrant, potent, pan-mutant IDH (miDH) inhibitor for use in miDH solid and hematologic malignancies, AACR-NCI-EORTC International Conference: Molecular Targets and Cancer Therapeutics (Oct. 26-30, 2017; Philadelphia, PA).
Yu, J. et al., Clinical implications of recurrent gene mutations in acute myeloid leukemia, Exp. Hematol. Oneal., 9:1-11 (2020).
Zhao, S. et al., Glioma-Derived Mutations in IDH1 Dominantly Inhibit IDH1 Catalytic Activity and Induce HIF-1a, Science, 324(5924): 261-265 (2009).
Zheng, B. et al., Crystallographic Investigation and Selective Inhibition of Mutant Isocitrate Dehydrogenase, ACS Medicinal Chemistry Letters, 4(6): 542-546 (2013).

\* cited by examiner

SOLID FORMS OF ((S)-5-((1-(6-CHLORO-2-OXO-1,2-DIHYDROQUINOLIN-3-YL)ETHYL)AMINO)-1-METHYL-6-OXO-1,6-DIHYDROPYRIDINE-2-CARBONITRILE

CROSS REFERENCE TO RELATED APPLICATIONS

This application is a continuation of U.S. application Ser. No. 17/183,606, filed Feb. 24, 2021, now U.S. Pat. No. 11,723,905, which was a continuation of U.S. application Ser. No. 16/693,642, filed Nov. 25, 2019, now U.S. Pat. No. 10,959,994, which is a continuation of U.S. application Ser. No. 16/414,716, filed May 16, 2019, now U.S. Pat. No. 10,532,047, which claims the benefit of and priority to U.S. provisional patent application No. 62/672,461, filed on May 16, 2018, U.S. provisional patent application No. 62/672,462, filed on May 16, 2018, and U.S. provisional patent application No. 62/692,591, filed on Jun. 29, 2018, the entire contents of which are incorporated herein by reference.

TECHNICAL FIELD

The present disclosure relates to pharmaceutical compositions, including a solid form of a certain compound useful for inhibiting mutant isocitrate dehydrogenase 1 (mIDH1).

BACKGROUND

The solid form of a compound may be important when the compound is used for pharmaceutical purposes. For example, compared with an amorphous solid, the solid physical properties of a crystalline compound may change from one solid form to another, which may affect its suitability for pharmaceutical use. In addition, different solid forms of a crystalline compound can incorporate different types and/or different amounts of impurities. The solid form of a compound can also affect chemical stability upon exposure to heat and/or water over a period of time.

The compound ((S)-5-((1-(6-chloro-2-oxo-1,2-dihydroquinolin-3-yl)ethyl)amino)-1-methyl-6-oxo-1,6-dihydropyridine-2-carbonitrile ("Compound 1")

Compound 1

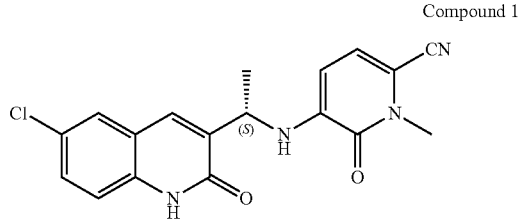

is an selective inhibitor of R132X mIDH-1. The free base of Compound 1 can be formulated into a pharmaceutical composition for treating patients diagnosed with a mIDH-1 form of cancer. The pharmaceutical composition can be provided in a unit dosage form (e.g., a capsule or unit dosage form) for oral use.

A preparation of a lyophilized solid form of Compound 1 is described in the publication WO2016/044789. However, therapeutic compounds often exist in a variety of solid forms having different properties. There remains a need for identifying solid forms of Compound 1 useful for various therapeutic applications.

SUMMARY

Crystalline ((S)-5-((1-(6-chloro-2-oxo-1,2-dihydroquinolin-3-yl)ethyl)amino)-1-methyl-6-oxo-1,6-dihydropyridine-2-carbonitrile (Compound 1), and methods of making compositions comprising crystalline Compound 1, are disclosed herein. In some embodiments, a novel solid form of Compound 1 disclosed herein includes Compound 1 in a solid form designated as Type A, as well as compositions comprising a solid form of Compound 1. Novel compositions also include Compound 1 as a solid form designated as Type A, and/or crystalline and amorphous solid forms of Compound 1. The various solid forms of Compound 1 can be identified by certain characteristic properties.

A preferred solid form of ((S)-5-((1-(6-chloro-2-oxo-1,2-dihydroquinolin-3-yl)ethyl)amino)-1-methyl-6-oxo-1,6-dihydropyridine-2-carbonitrile (Compound 1) can be characterized by a reflection X-ray powder diffraction (XRPD) pattern comprising characteristic peaks at 6.3, 12.8, 13.8, 23.6, and 27.8 degrees±0.2° 2θ.

DETAILED DESCRIPTION

Figure 1:
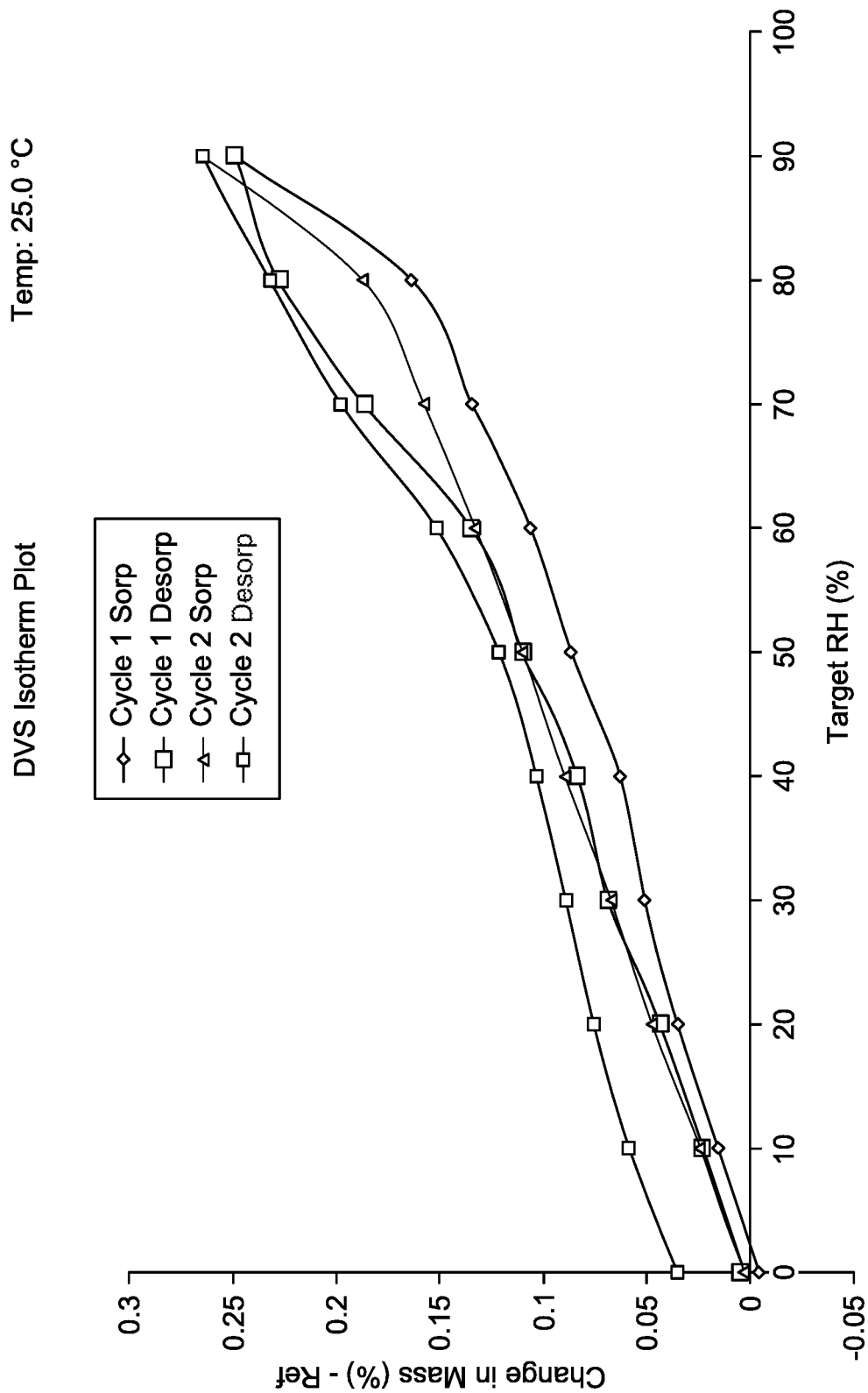
FIG. 1 depicts a dynamic vapor sorption (DVS) isotherm plot of Compound 1 Type A solid form.

The bioactive chemical ((S)-5-((1-(6-chloro-2-oxo-1,2-dihydroquinolin-3-yl)ethyl)amino)-1-methyl-6-oxo-1,6-dihydropyridine-2-carbonitrile can be prepared as a solid form. The compound ((S)-5-((1-(6-chloro-2-oxo-1,2-dihydroquinolin-3-yl)ethyl)amino)-1-methyl-6-oxo-1,6-dihydropyridine-2-carbonitrile ("Compound 1") is shown below:

Compound 1

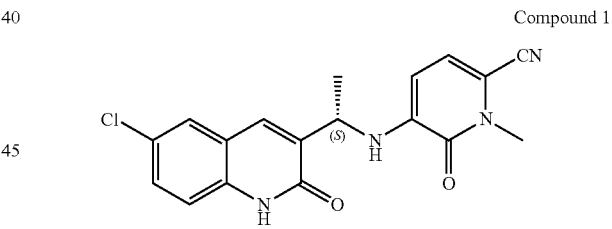

Compound 1 can also be referred to as olutasidenib, CAS No.: 1887014-12-1, (S)-5-((1-(6-chloro-2-oxo-1,2-dihydroquinolin-3-yl)ethyl)amino)-1-methyl-6-oxo-1,6-dihydropyridine-2-carbonitrile, or 5-{[(1S)-1-(6-chloro-2-oxo-1,2-dihydroquinolin-3-yl)ethyl]amino}-1-methyl-6-oxo-1,6-dihydropyridine-2-carbonitrile.

Compound 1 can occur in an amorphous solid form or in a crystalline solid form or in mixtures of solid forms. Crystalline solid forms of Compound 1 can exist in one or more unique solid forms, which can additionally comprise one or more equivalents of water or solvent (i.e., hydrates or solvates, respectively).

As disclosed herein, crystalline form(s) of Compound 1 have distinct characteristic XRPD peaks (see Example 2) that are not characterized in previous disclosures of Compound 1. Accordingly, provided herein are crystalline Compound 1 solid forms, pharmaceutical compositions thereof, and methods of preparing those crystalline Compound 1 solid forms and methods of use thereof.

A novel Compound 1 solid form can be obtained by a method reported in Example 2. For example, Compound 1 Type A can be prepared by a solution comprising Compound 1 and a solvent, and concentrating the solution, then diluting the solution with a solvent, stirring the solution for a period of time and cooling the solution to precipitate a crystalline solid of Compound 1 Type A. In some embodiments, the solution is stirred at room temperature. In some embodiments, the solution is cooled to a temperature of about 0° C. In some embodiments, the solvent comprises ethyl acetate.

As used herein, the term "precipitate" refers to the formation of a solid substance from a solution containing the same substance. A substance which precipitates from solution may be amorphous or crystalline. Precipitation may occur under a variety of conditions known to those of skill in the art, including the treatment of a solution of a solute (e.g., solute A in solvent B) with an antisolvent (i.e., a solvent that is miscible with solvent B, but does not dissolve solute A).

Solid forms of Compound 1 can be identified by various analytical techniques, such as X-ray powder diffraction (XRPD). Solid forms of Compound 1 disclosed herein include Compound 1 Type A solid form, as well as compositions comprising a solid form of Compound 1 comprising Type A solid form.

A novel Compound 1 Type A solid form is characterized by an X-ray Powder Diffraction (XRPD) pattern, having diffraction peaks at angles (2 theta±0.2) of 6.3, 12.8, 13.8, 23.6, and 27.8. In some embodiments, a novel Compound 1 Type A is characterized by an X-ray Powder Diffraction (XRPD) pattern, having diffraction peaks at angles (2 theta±0.2) of 6.3, 12.8, 13.8, 23.6, and 27.8, corresponding to d-spacing (angstroms±0.2) of 14.0, 6.9, 6.4, 3.8, and 3.2, respectively. In some embodiments, Compound 1 Type A can be identified by X-ray Powder Diffraction (XRPD) pattern, having characteristic diffraction peaks at angles (2 theta±0.2) of 5.7, 6.3, 8.5, 10.6, 12.8, 13.8, 17.3, 22.0, 22.8, 23.6, and 27.8. In some embodiments, Compound 1 Type A can be identified by X-ray Powder Diffraction (XRPD) pattern, having characteristic diffraction peaks at angles (2 theta±0.2) of 5.7, 6.3, 8.5, 10.6, 12.8, 13.8, 17.3, 22.0, 22.8, 23.6, and 27.8, corresponding to d-spacing (angstroms±0.2) of 15.4, 14.0, 8.4, 6.9, 6.4, 5.1, 4.0, 3.9, 3.8, and 3.2, respectively.

In some embodiments, Compound 1 Type A solid form is characterized by an X-ray powder diffraction having peaks at the same or substantially the same angles (2θ±0.2) and corresponding d-spacing (Å±0.2) of:

| 2θ ± 0.2 | d-spacing Å ± 0.2 |
| --- | --- |
| 5.7 | 15.4 |
| 6.3 | 14.0 |
| 8.5 | 10.4 |
| 10.6 | 8.4 |
| 11.4 | 7.8 |
| 12.8 | 6.9 |
| 13.8 | 6.4 |
| 14.2 | 6.2 |
| 15.2 | 5.8 |
| 15.6 | 5.7 |
| 17.3 | 5.1 |
| 17.9 | 5.0 |
| 18.2 | 4.9 |
| 18.9 | 4.7 |
| 19.6 | 4.5 |
| 20.6 | 4.3 |
| 21.5 | 4.1 |
| 22.0 | 4.0 |
| 22.8 | 3.9 |
| 23.6 | 3.8 |
| 24.5 | 3.6 |
| 24.8 | 3.6 |
| 25.3 | 3.5 |
| 25.6 | 3.5 |
| 26.0 | 3.4 |
| 26.3 | 3.4 |
| 27.0 | 3.3 |
| 27.8 | 3.2 |
| 28.9 | 3.1 |
| 30.0 | 3.0 |
| 31.2 | 3.0 |
| 32.1 | 2.8 |
| 33.6 | 2.7 |
| 34.1 | 2.6 |
| 36.3 | 2.5 |
| 37.0 | 2.4 |
| 38.1 | 2.4 |

The presence of Compound 1 in the Type A solid form can be identified by one or more techniques, including DSC, TGA, DVS and XRPD. In some embodiments, Compound 1 Type A solid form is characterized by a differential scanning calorimetry (DSC) endotherm having a minima at about 256.64° C. The dynamic vapor sorption (DVS) isotherm plot of FIG. 1, the differential scanning calorimetry (DSC) thermogram of FIG. 2, the thermogravimetric analysis (TGA) plot in FIG. 3 and the X-ray Powder Diffraction (XRPD) pattern in FIG. 4 were each obtained by a composition comprising Compound 1, Type A solid form. The presence of Compound 1 Type A solid form can be identified by performing DSC, TGA, DVS and/or XRPD analysis of a composition and identifying sufficient similarity in comparison with the DVS isotherm plot in FIG. 1, the DSC thermogram in FIG. 2, the TGA plot in FIG. 3 and/or the XRPD pattern of FIG. 4.

In some embodiments, a pharmaceutical composition can comprise, and/or be obtained from, Compound 1 Type A solid form characterized by a dynamic vapor sorption (DVS) isotherm plot substantially similar to FIG. 1. In some embodiments, a pharmaceutical composition can comprise, and/or be obtained from, Compound 1 Type A solid form characterized by a differential scanning calorimetry (DSC) thermogram substantially similar to FIG. 2. In some embodiments, a pharmaceutical composition can comprise, and/or be obtained from, Compound 1 Type A solid form characterized by a thermogravimetric analysis (TGA) plot substantially similar to FIG. 3. In some embodiments, a pharmaceutical composition can comprise, and/or be obtained from, Compound 1 Type A solid form characterized by an X-ray Powder Diffraction (XRPD) pattern substantially similar to FIG. 4.

In some embodiments, the present disclosure provides a composition comprising amorphous and crystalline solid forms of Compound 1. In some embodiments, the composition comprises crystalline Compound 1 and amorphous Compound 1, wherein the amorphous Compound 1 is present in an amount selected from the following ranges: 90-99%, 80-90%, 70-80%, 60-70%, 50-60%, 40-50%, 30-40%, 20-30%, 10-20%, 1-10% and 0-1%.

In some embodiments, the present disclosure provides a pharmaceutical composition such as a drug product or drug substance comprising a solid form of Compound 1 disclosed herein. In some embodiments, the present disclosure provides a pharmaceutical composition comprising crystalline solid Type A of Compound 1. For example, a pharmaceutical composition can comprise, and/or be obtained from, the solid form of Compound 1 designated as Type A solid form of Compound 1 and is characterized by an X-ray Powder Diffraction (XRPD) pattern, having characteristic diffraction peaks at angles (2 theta±0.2) of 6.3, 12.8, 13.8, 23.6, and 27.8. In some embodiments, a pharmaceutical composition can comprise, and/or be obtained from, the solid form of Compound 1 designated as Type A of Compound 1 and is characterized by an XRPD pattern having characteristic diffraction peaks at angles (2 theta±0.2) of 5.7, 6.3, 8.5, 10.6, 12.8, 13.8, 17.3, 22.0, 22.8, 23.6, and 27.8. In some embodiments, a pharmaceutical composition can comprise, and/or be obtained from, the solid form of Compound 1 Type A and is characterized by an X-ray Powder Diffraction (XRPD) pattern, having diffraction peaks at angles (2 theta±0.2) of 6.3, 12.8, 13.8, 23.6, and 27.8, corresponding to d-spacing (angstroms±0.2) of 14.0, 6.9, 6.4, 3.8, and 3.2, respectively. In some embodiments, a pharmaceutical composition can comprise, and/or be obtained from, the solid form of Compound 1 Type A and can be identified by X-ray Powder Diffraction (XRPD) pattern, having characteristic diffraction peaks at angles (2 theta±0.2) of 5.7, 6.3, 8.5, 10.6, 12.8, 13.8, 17.3, 22.0, 22.8, 23.6, and 27.8, corresponding to d-spacing (angstroms±0.2) of 15.4, 14.0, 8.4, 6.9, 6.4, 5.1, 4.0, 3.9, 3.8, and 3.2, respectively.

In some embodiments, a pharmaceutical composition can comprise, and/or be obtained from, the solid form of Compound 1 designated as Type A of Compound 1 and is characterized by an XRPD pattern having peaks at substantially the same angles (2θ±0.2) and corresponding d-spacing (Å±0.2) of:

| 2θ ± 0.2 | d-spacing Å ± 0.2 |
|---|---|
| 5.7 | 15.4 |
| 6.3 | 14.0 |
| 8.5 | 10.4 |
| 10.6 | 8.4 |
| 11.4 | 7.8 |
| 12.8 | 6.9 |
| 13.8 | 6.4 |
| 14.2 | 6.2 |
| 15.2 | 5.8 |
| 15.6 | 5.7 |
| 17.3 | 5.1 |
| 17.9 | 5.0 |
| 18.2 | 4.9 |
| 18.9 | 4.7 |
| 19.6 | 4.5 |
| 20.6 | 4.3 |
| 21.5 | 4.1 |
| 22.0 | 4.0 |
| 22.8 | 3.9 |
| 23.6 | 3.8 |
| 24.5 | 3.6 |
| 24.8 | 3.6 |
| 25.3 | 3.5 |
| 25.6 | 3.5 |
| 26.0 | 3.4 |
| 26.3 | 3.4 |
| 27.0 | 3.3 |
| 27.8 | 3.2 |
| 28.9 | 3.1 |
| 30.0 | 3.0 |
| 31.2 | 3.0 |
| 32.1 | 2.8 |
| 33.6 | 2.7 |
| 34.1 | 2.6 |
| 36.3 | 2.5 |

-continued

| 2θ ± 0.2 | d-spacing Å ± 0.2 |
|---|---|
| 37.0 | 2.4 |
| 38.1 | 2.4 |

Pharmaceutical compositions reported herein can be combined with a pharmaceutically acceptable carrier or excipient. In some embodiments, pharmaceutical compositions reported herein can be provided in a unit dosage form container (e.g., in a vial or bag or the like). In some embodiments, pharmaceutical compositions reported herein can be provided in an oral dosage form.

In some embodiments, the pharmaceutical composition comprises an active pharmaceutical ingredient (API) comprising, consisting essentially of, or consisting of Compound 1 prepared under applicable Good Manufacturing Practice (GMP). For example, the pharmaceutical composition can be a batch composition comprising Compound 1 (preferably including Solid Form Type A of Compound 1), wherein the batch composition adheres to Good Manufacturing Practices (e.g., ICH Harmonised Tripartite Guideline, Good Manufacturing Practice Guide for Active Pharmaceutical Ingredients Q7, Current Step 4 version dated 10 Nov. 2010). More preferably, the GMP batch composition can be a homogenous blended batch comprising Type A Solid Form of Compound 1. The FDA (Food and Drug Administration) provides applicable guidance on Good Manufacturing Practice (GMP) for the manufacturing of active pharmaceutical ingredients (APIs) under an appropriate system for managing quality. As used with respect to manufacture of API under GMP, "manufacturing" is defined to include all operations of receipt of materials, production, packaging, repackaging, labelling, relabelling, quality control, release, storage and distribution of APIs and the related controls. An "API Starting Material" is a raw material, intermediate, or an API that is used in the production of an API and that is incorporated as a significant structural fragment into the structure of the API. An API Starting Material can be an article of commerce, a material purchased from one or more suppliers under contract or commercial agreement, or produced in-house. API Starting Materials normally have defined chemical properties and structure.

In some embodiments, an oral dosage form of Compound 1 Type A can be a capsule. In some embodiments, an oral dosage form of Compound 1 Type A is a tablet. In some embodiments, an oral dosage form comprises a filler. In some embodiments, an oral dosage form comprises two fillers. In some embodiments, an oral dosage form comprises one or more fillers. In some embodiments, the filler is selected from the group consisting of Avicel PH101 (50 μm) and Avicel PH102 (100 μm). In some embodiments, an oral dosage form comprises one or more disintegrants. In some embodiments a disintegrant is Ac-Di-Sol. In some embodiments, the oral dosage form comprises one or more lubricants. In some embodiments, the lubricant is magnesium stearate. In some embodiments, an oral dosage form comprises one or more glidants, anti-adherents and/or anti-statics. In some embodiments, the glidant, anti-adherent and/or anti-static is colloidal silicon dioxide. In some embodiments, an oral dosage form is prepared via dry blending. In some embodiments, an oral dosage form is a tablet and is prepared via dry granulation.

In some embodiments, the present disclosure provides methods of inhibiting mutant isocitrate dehydrogenase 1

(mIDH1), comprising administering a solid form of Compound 1 to a subject. In some embodiments, the present disclosure provides methods of treating a disease, disorder, or condition responsive to inhibition of mutant isocitrate dehydrogenase 1 (mIDH1), comprising administering a solid form of Compound 1 (e.g., Compound 1 as a Type A solid form) to a subject in need thereof. In some embodiments, the disease, disorder, or condition is associated with mutant isocitrate dehydrogenase.

In some embodiments, the present disclosure provides methods of treating cancer comprising administering a solid form of Compound 1 (e.g., Compound 1 as a Type A solid form) to a subject in need thereof. In some embodiments, the present disclosure provides methods of reducing 2-hydroxyglutarate comprising administering a solid form of Compound 1 (e.g., Compound 1 as a Type A solid form) to a subject in need thereof. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent, delay or lessen the severity of their recurrence.

EXAMPLES

Instrumentation and Methods

Unless otherwise indicated, the following instrumentation and methods were used in the working examples described herein.

Unless otherwise noted, reagents and solvents were used as received from commercial suppliers. Proton nuclear magnetic resonance (NMR) spectra were obtained on either Bruker or Varian spectrometers at 300 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). High performance liquid chromatograph (HPLC) analyses were obtained using a XBridge Phenyl or C18 column (5 μm, 50×4.6 mm, 150×4.6 mm or 250×4.6 mm) with UV detection (Waters 996 PDA) at 254 nm or 223 nm using a standard solvent gradient program (Methods 1-2).

LCMS Method 1 (ESI, 4 Min Method):
Instruments and Conditions:

| HPLC: Waters HT2790 Alliance UV: Waters 996 PDA | MS: Waters ZQ Single Quad Mass Spectrometer |
|---|---|

Conditions:

| | |
|---|---|
| Mobile phase A | 95% water/5% methanol with 0.1% Formic Acid |
| Mobile phase B (B) | 95% methanol/5% water with 0.1% Formic Acid |
| Column | XBridge Phenyl or C18, 5 μm 4.6 × 50 mm |
| Column temperature | Ambient |
| LC gradient | Linear 5-95% B in 2.5 min, hold 95% B to 3.5 min |
| LC Flow rate | 3 mL/min |
| UV wavelength | 220 nm and 254 nm |
| Ionization Mode | Electrospray Ionization; positive/negative |

LCMS Method 2: (APCI, 20 Min)
Instruments and Conditions:

HPLC-Agilent 1100 series.
Column: Agela Technologies Durashell C18, 3 μm, 4.6 × 50 mm,).
Mobile Phase A: ACN + 0.1% TFA.
Mobile Phase B: Water + 0.1% TFA.

| Gradient: | Time (min) | % B |
|---|---|---|
| | 00 | 95 |
| | 15 | 05 |
| | 18 | 05 |
| | 20 | 95 |

Flow Rate: 1 mL/min.
ColumnTemperature: Ambient.
Detector: 254 nm.

X-Ray Powder Diffraction (XRPD)

High resolution X-ray Powder Diffraction experiments were performed with a Panalytical X'Pert$^3$ Powder X-ray diffractometer on a Si zero-background holder. The 2θ position was calibrated against Panalytical 640 Si powder standard. Details of the XRPD method are listed below:

| Parameters for Reflection Mode | |
|---|---|
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0131 |
| Scan speed (°/s) | 0.033 |

Peaks are reported as diffraction angles at 2 theta, with d-spacing measured in angstroms.

Thermal Analysis

Thermo gravimetric analysis (TGA) experiments were performed on TA Q500 TGA from TA Instruments. Samples were heated at 10° C./min from about 20° C. to about 300° C. using dry nitrogen to purge the system. The details of the method are provided below:

| Parameters | TGA |
|---|---|
| Pan Type | Platinum plate, open |
| Temperature | RT-250° C. |
| Ramp rate | 10° C./min |
| Purge gas | $N_2$ |

Differential scanning calorimetry (DSC) experiments were performed on a TA Q2000 DSC from TA Instruments. Samples were heated at 10° C./min from about 20° C. to about 300° C. using dry nitrogen to purge the system. The details of the method are provided below:

| Parameters | DSC |
|---|---|
| Pan Type | Aluminum pan, closed |
| Temperature | RT-250° C. |
| Ramp rate | 10° C./min |
| Purge gas | N₂ |

Dynamic Vapor Sorption

Dynamic vapor sorption (DVS) was obtained using a Surface Measurement Systems (SMS) DVS Intrinsic. The details of the method are provided below:

| Parameters | Values |
|---|---|
| Temperature | 25° C. |
| Sample size | 10-20 mg |
| Gas and flow rate | N₂, 200 mL/min |
| dm/dt | 0.002%/min |
| Min. dm/dt stability duration | 10 min |
| Max. equilibrium time | 360 min |
| RH range | 20% RH - 95% RH-0% RH-95% RH |
| RH step size | 10% (90% RH-0% RH-90% RH) |
|  | 5% (95% RH-90% RH and 90% RH-95% RH) |

Example 1—Synthesis of (S)-5-((1-(6-chloro-2-oxo-1,2-dihydroquinolin-3-yl)ethyl)amino)-1-methyl-6-oxo-1,6-dihydropyridine-2-carbonitrile (Compound 1)

Intermediate 1: (S)-3-(1-aminoethyl)-6-chloroquinolin-2(1H)-one hydrochloride

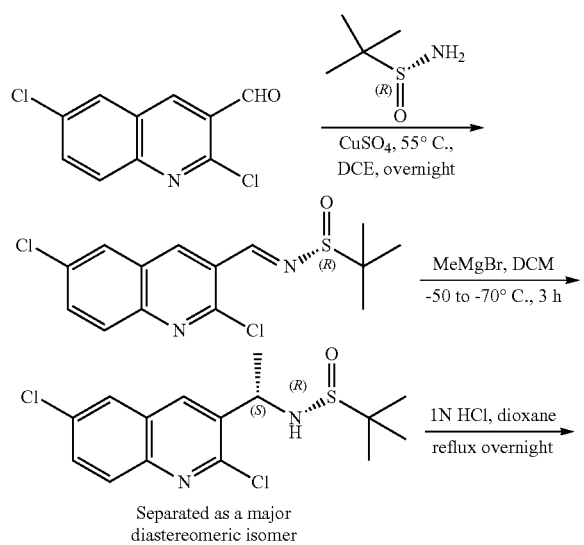

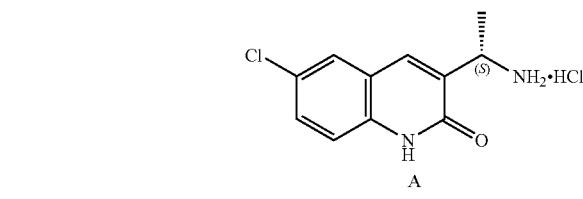

Step-1: (R,E)-N-((2,6-dichloroquinolin-3-yl)methylene)-2-methylpropane-2-sulfinamide

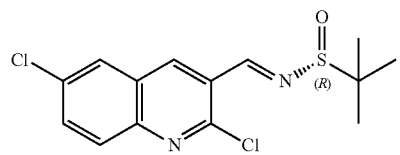

To a mixture of 2,6-dichloroquinoline-3-carbaldehyde (15.0 g, 66.37 mmol) and (R)-2-methylpropane-2-sulfinamide (8.85 g, 73.14 mmol) in 1,2-dichloroethane (150 mL) was added CuSO₄ (16.0 g, 100.25 mmol). The resulting mixture was heated to 55° C. and stirred at 55° C. overnight. After TLC and MS showed complete disappearance of starting materials, the mixture was cooled to room temperature and filtered through a pad of Celite®. The pad of Celite® was then rinsed with CH₂Cl₂. The filtrate was evaporated to dryness in vacuo and purified by SiO₂ column chromatography (0 to 25% hexanes/EtOAc) to afford the title compound, (R,E)-N-((2,6-dichloroquinolin-3-yl)methylene)-2-methylpropane-2-sulfinamide, as a yellow solid (17.7 g, 81% yield).

Step-2: (R)—N—((S)-1-(2,6-dichloroquinolin-3-yl)ethyl)-2-methylpropane-2-sulfinamide

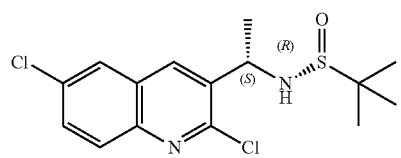

To a solution of (R,E)-N-((2,6-dichloroquinolin-3-yl)methylene)-2-methylpropane-2-sulfinamide (8.85 g, 26.88 mmol) in anhydrous CH₂Cl₂ (200 mL) at −60° C. was added dropwise MeMgBr (3M solution in diethyl ether, 13.5 mL, 40.54 mmol). The resulting reaction mixture was stirred at about −60 to −50° C. for 3 hours and then stirred at −20° C. overnight under an atmosphere of N₂. After TLC and MS showed complete disappearance of starting materials, saturated NH₄Cl (163 mL) was added at −20° C. and the resulting mixture was stirred for 10 minutes. The aqueous phase was extracted with CH₂Cl₂ (100 mL×3), dried over anhydrous Na₂SO₄, filtered, and evaporated. The residue was purified by column chromatography on an ISCO® chromatography system (SiO₂: Gold column; gradient; hexanes to 100% EtOAc) to provide the title compound, (R)—N—((S)-1-(2,6-dichloroquinolin-3-yl)ethyl)-2-methylpropane-2-sulfinamide, as a yellow solid (5.8 g, 63% yield).

Step-3: (S)-3-(1-aminoethyl)-6-chloroquinolin-2(1B)-one hydrochloride (A)

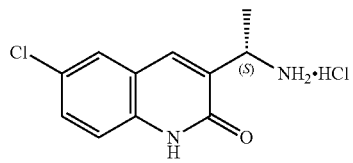

A mixture of (R)—N—((S)-1-(2,6-dichloroquinolin-3-yl)ethyl)-2-methylpropane-2-sulfinamide (6.6 g, 19.13 mmol) in 1,4-dioxane (41 mL) and 1N HCl (41 mL) was heated at reflux overnight. The solvents were evaporated in vacuo and the resulting residue was dissolved in hot water and lyophilized. The crude product was triturated with diethyl ether to afford the title compound A as a yellow solid (9.0 g, ee: 98.4%). $^1$H NMR (300 MHz, DMSO-$d_6$): δ ppm 12.4 (br s, 1H), 8.32 (br s, 2H), 8.07 (s, 1H), 7.85 (d, J=2.2 Hz, 1H), 7.63 (dd, J1=8.8 Hz, J2=2.5 Hz, 1H), 7.40 (d, J=8.8 Hz, 1H), 4.40-4.45 (m, 1H), 1.53 (d, J=8.5 Hz, 3H). LCMS (Method 2): Rt 3.42 min, m/z 223.1 [M+H]$^+$.

Intermediate 2: 5-fluoro-1-methyl-6-oxo-1,6-dihydropyridine-2-carbonitrile

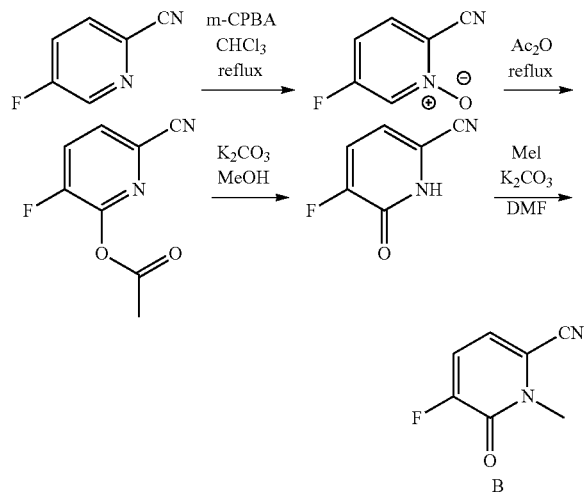

Step-1: 2-cyano-5-fluoropyridine 1-oxide

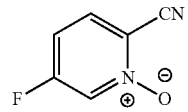

A solution of 5-fluoropicolinonitrile (7.27 g, 59.5 mmol) in CHCl$_3$ (60 mL) was added dropwise by addition funnel to a solution of m-CPBA (<77%, 22.00 g, 98 mmol) in CHCl3 160 mL). The solution was stirred at reflux for 4 days, at which time LCMS showed ~85% conversion. The sample was allowed to cool, then sodium sulfite (12.4 g, 98 mmol) was added and the sample was stirred at room temperature for three hours, during which time the solution became thick with a white precipitate. The sample was diluted with DCM (300 mL) and filtered on a Buchner funnel, and the filter cake was washed with DCM (~400 mL). A white material precipitated in the filtrate. The filtrate mixture was washed with saturated aqueous NaHCO$_3$ (400 mL), during which the solids went into solution. The organic layer was washed with water (300 mL), then dried (MgSO$_4$) and filtered. Silica gel was added and the mixture was evaporated under reduced pressure. The material was chromatographed by Biotage MPLC (340 g silica gel column) with 0 to 100% EtOAc in hexanes, with isocratic elution when peaks came off to provide 2-cyano-5-fluoropyridine 1-oxide (4.28 g, 31.0 mmol, 52% yield) as a white solid. $^1$H NMR (300 MHz, DMSO-$d_6$): δ ppm 8.85-8.93 (m, 1H), 8.23 (dd, J=9.09, 6.74 Hz, 1H), 7.53-7.64 (m, 1H). LCMS (Method 1): Rt 0.57 min., m/z 138.9 [M+H]$^+$.

Step 2: 6-cyano-3-fluoropyridin-2-yl acetate

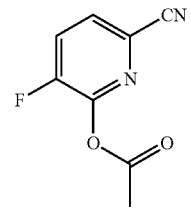

A solution of 2-cyano-5-fluoropyridine 1-oxide (4.28 g, 31.0 mmol) in acetic anhydride (40 ml, 424 mmol) was heated at reflux (150° C. bath) for three days, during which the clear solution turned dark. The sample was concentrated under reduced pressure. The residue was dissolved in MeOH (30 mL) and stirred for 1 hour. Silica gel was added and the solvent was evaporated under reduced pressure. The material was chromatographed by Biotage MPLC (100 g silica gel column) with 0 to 23% EtOAc in hexanes to provide 6-cyano-3-fluoropyridin-2-yl acetate (3.32 g, 18.43 mmol, 60% yield) as a clear liquid that solidified on cooling. $^1$H NMR (300 MHz, CHLOROFORM-d): δ ppm 7.65-7.75 (m, 2H), 2.42 (s, 3H). LCMS (Method 1): Rt 1.54 min., m/z 138.8 (loss of acetate).

Step 3: 5-fluoro-6-oxo-1,6-dihydropyridine-2-carbonitrile

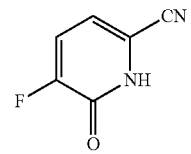

A solution of 6-cyano-3-fluoropyridin-2-yl acetate (3.32 g, 18.43 mmol) in MeOH (40 ml) was treated with potassium carbonate (5.10 g, 36.9 mmol) and stirred at room temperature for four hours. LCMS at 2 hours showed the reaction had gone to completion. The solvent was evaporated under reduced pressure. The residue was dissolved in water (100 mL) and acidified to pH≤1 with 1M HCl. The solution was extracted with EtOAc (3×100 mL). The combined organic extracts were dried (Na₂SO₄), filtered, and evaporated under reduced pressure to provide 5-fluoro-6-oxo-1,6-dihydropyridine-2-carbonitrile (2.34 g, 16.94 mmol, 92% yield) as a white solid. ¹H NMR (300 MHz, DMSO-d₆): δ ppm 12.92 (br s, 1H), 7.73 (br s, 1H), 7.43 (br s, 1H). LCMS (Method 1): Rt 0.70 min., m/z 138.9 [M+H]⁺.

Step 4: 5-fluoro-1-methyl-6-oxo-1,6-dihydropyridine-2-carbonitrile (B)

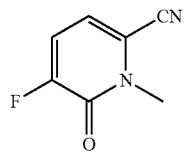

A mixture of 5-fluoro-6-oxo-1,6-dihydropyridine-2-carbonitrile (2.31 g, 16.73 mmol) and potassium carbonate (4.86 g, 35.2 mmol) in a 200 mL round bottom flask was treated with DMF (46 mL) and stirred for 15 minutes. MeI (1.2 mL, 19.19 mmol) was added and the mixture was stirred at room temperature for 45 minutes. The solvent was evaporated under reduced pressure. The residue was mixed with water (150 mL) and extracted with DCM (2×150 mL). The combined organic extracts were dried (MgSO₄), filtered, treated with silica gel, and evaporated under reduced pressure, then evaporated further at 60° C. under high vacuum. The material was chromatographed by Biotage MPLC with 0 to 35% EtOAc in hexanes, with isocratic elution at 16% EtOAc and 35% EtOAc while peaks were eluted. The peak that was eluted with 16% EtOAc was O-methylated material and was discarded. The peak that was eluted with 35% EtOAc provided the title compound B (1.70 g, 11.17 mmol, 67% yield) as a solid. ¹H NMR (300 MHz, DMSO-d₆): δ ppm 7.53 (dd, J=9.38, 7.62 Hz, 1H), 7.18 (dd, J=7.77, 4.84 Hz, 1H), 3.60 (s, 3H). LCMS (Method 1): Rt 0.94 min., m/z 152.9 [M+H]⁺.

Step 5: (S)-5-((1-(6-chloro-2-oxo-1,2-dihydroquinolin-3-yl)ethyl)amino)-1-methyl-6-oxo-1,6-dihydropyridine-2-carbonitrile (Compound 1)

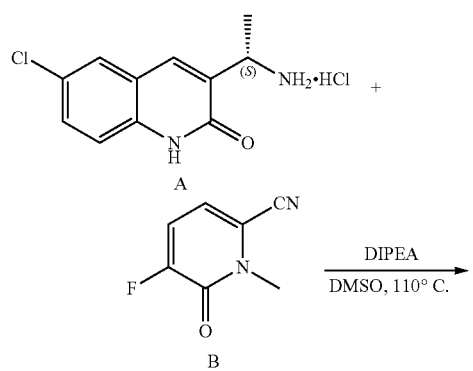

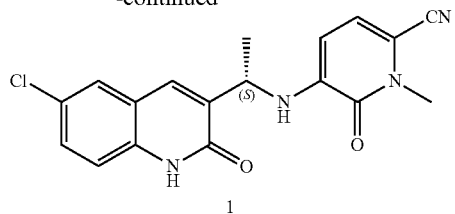

A mixture of 5-fluoro-1-methyl-6-oxo-1,6-dihydropyridine-2-carbonitrile B (1.23 g, 8.09 mmol), (S)-3-(1-aminoethyl)-6-chloroquinolin-2(1H)-one hydrochloride A (1.91 g, 7.37 mmol) and N,N-diisopropylethylamine (3.8 mL, 21.8 mmol) in anhydrous dimethyl sulfoxide (57 mL) under N₂ was heated to 110° C. and stirred for 6 hours. After cooling to room temperature, the mixture was partitioned between EtOAc/H₂O (750 mL/750 mL). The organic layer was separated, dried (Na₂SO₄), and concentrated in vacuum. The residue was purified on an ISCO® chromatography system twice (40 g silica gel column, EtOAc/hexanes 0-100%; 80 g silica gel column, MeOH/dichloromethane 0~5%). The colorless fractions were combined and dichloromethane was removed under reduced pressure on rotavap until a lot of white solid precipitated out. The white solid was collected by filtration and washed with cold MeOH. It was then mixed with MeCN/H₂O (10 mL/25 mL) and lyophilized to afford the title compound 1 as a white solid (790 mg). m.p. 262-264° C. ¹H NMR (300 MHz, DMSO-d₆) δ: 12.07 (s, 1H), 7.75 (s, 1H), 7.73 (d, J=2.2 Hz, 1H), 7.51 (dd, J=8.6, 2.3 Hz, 1H), 7.31 (d, J=8.8 Hz, 1H), 6.97 (d, J=8.0 Hz, 1H), 6.93 (d, J=7.7 Hz, 1H), 5.95 (d, J=8.0 Hz, 1H), 4.68 (m, 1H), 3.58 (s, 3H), 1.50 (d, J=6.6 Hz, 3H). LCMS (Method 2): 100% pure @ 254 nm, Rt 10.78 min, m/z 355, 357 [M+H]+. The filtrate and the colored fractions (TLC pure) from the second ISCO were combined and treated with activated charcoal and filtered (until the filtrate is colorless). The filtrate was then concentrated under reduced pressure on rotavap to remove dichloromethane until a lot of white solid precipitated out. The white solid was collected by filtration and washed with cold MeOH. It was then mixed with MeCN/H₂O (10 mL/25 mL) and lyophilized to afford the title compound 1 as a white solid (970 mg). m.p. 262-264° C. ¹H NMR (300 MHz, DMSO-d₆) δ: 12.06 (s, 1H), 7.75 (s, 1H), 7.73 (d, J=2.5 Hz, 1H), 7.51 (dd, J=8.6, 2.3 Hz, 1H), 7.31 (d, J=8.8 Hz, 1H), 6.97 (d, J=8.0 Hz, 1H), 6.92 (d, J=8.0 Hz, 1H), 5.95 (d, J=8.0 Hz, 1H), 4.68 (m, 1H), 3.58 (s, 3H), 1.50 (d, J=6.9 Hz, 3H). LCMS (Method 2): 100% pure @ 254 nm, m/z 355, 357 [M+H]+.

Example 2—Solid form of (S)-5-((1-(6-chloro-2-oxo-1,2-dihydroquinolin-3-yl)ethyl)amino)-1-methyl-6-oxo-1,6-dihydropyridine-2-carbonitrile Compound 1 can be prepared via the method described in Example 1. Compound 1 was dissolved in 18 volumes of dichloromethane (all volumes are with respect to the quantity of compound 1 (v/w)). The resulting solution was then concentrated under reduced pressure to approximately 5 volumes. To the mixture was added 5 volumes of ethyl acetate. The mixture was concentrated under reduced pressure to 5 volumes. To the mixture was added an additional 5 volumes of ethyl acetate, and the mixture again concentrated under reduced pressure to 5 volumes. The mixture was diluted to 10 volumes with ethyl acetate, and the mixture stirred at room temperature for 18 hours and then cooled to 0° C. The mixture was stirred at 0° C. for 3 hours and then filtered. The solids were rinsed with ethyl acetate and dried under vacuum (counterbalanced by nitrogen) at ambient temperature.

The crystalline solid was determined to be the solid form of Compound 1 Type A. The DVS Isotherm of Compound 1 Type A is shown in FIG. 1. DVS shows maximum water uptake of 0.25% w/w at 25° C./90% RH, indicating that Compound 1 Type A is not hygroscopic.

Figure 2:
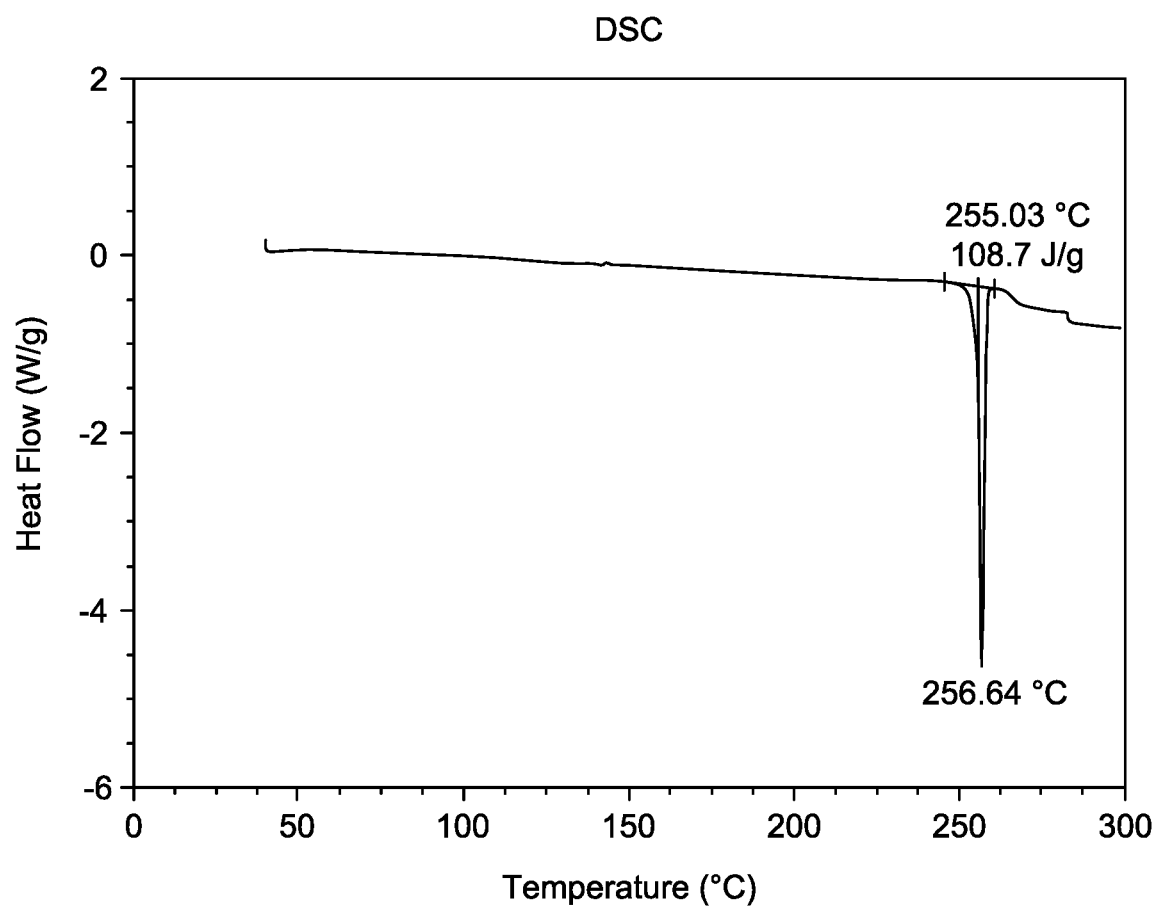
FIG. 2 depicts a differential scanning calorimetry (DSC) thermogram for Compound 1 Type A solid form.
Figure 3:
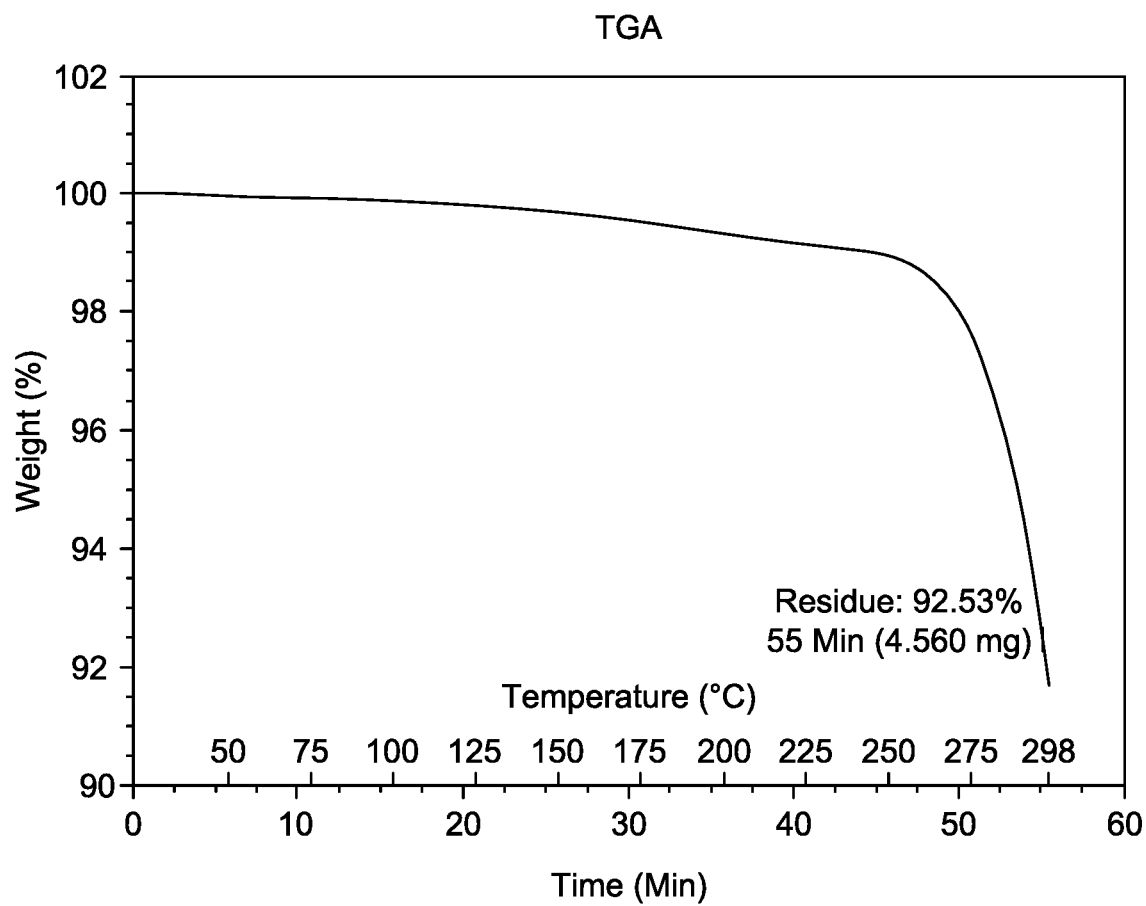
FIG. 3 depicts a thermogravimetric analysis (TGA) curve for Compound 1 Type A solid form.

The thermal behavior Compound 1 Type A was evaluated using DSC. An endothermic event was observed at 256.6° C. (peak max). The onset temperature and heat of fusion were 255.0° C. and 108.7 J/g respectively (FIG. 2).

TGA data (FIG. 3) do not show significant release of moisture or nonaqueous residual volatiles from Compound 1 Type A.

Figure 4:
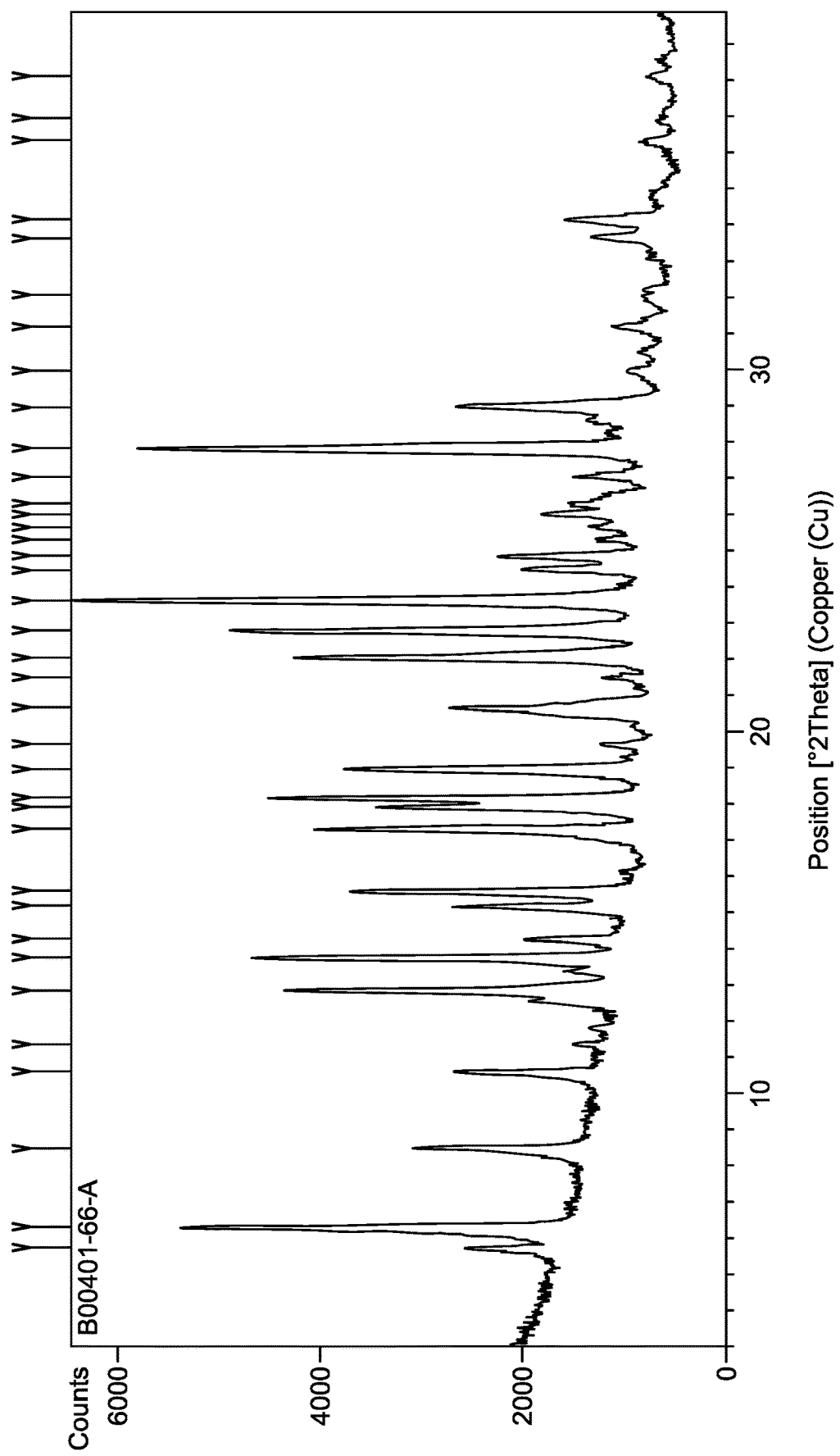
FIG. 4 depicts X-ray powder diffraction (XRPD) pattern of Compound 1 Type A solid form.

The X-ray powder diffraction pattern of the crystalline Compound 1 Type A is depicted in FIG. 4, and the corresponding data is summarized in Table 2-1:

TABLE 2-1

| 2 theta ± 0.2 | d-spacing Å ± 0.2 |
|---|---|
| 5.7 | 15.4 |
| 6.3 | 14.0 |
| 8.5 | 10.4 |
| 10.6 | 8.4 |
| 11.4 | 7.8 |
| 12.8 | 6.9 |
| 13.8 | 6.4 |
| 14.2 | 6.2 |
| 15.2 | 5.8 |
| 15.6 | 5.7 |
| 17.3 | 5.1 |
| 17.9 | 5.0 |
| 18.2 | 4.9 |
| 18.9 | 4.7 |
| 19.6 | 4.5 |
| 20.6 | 4.3 |
| 21.5 | 4.1 |
| 22.0 | 4.0 |
| 22.8 | 3.9 |
| 23.6 | 3.8 |
| 24.5 | 3.6 |
| 24.8 | 3.6 |
| 25.3 | 3.5 |
| 25.6 | 3.5 |
| 26.0 | 3.4 |
| 26.3 | 3.4 |
| 27.0 | 3.3 |
| 27.8 | 3.2 |
| 28.9 | 3.1 |
| 30.0 | 3.0 |
| 31.2 | 3.0 |
| 32.1 | 2.8 |
| 33.6 | 2.7 |
| 34.1 | 2.6 |
| 36.3 | 2.5 |
| 37.0 | 2.4 |
| 38.1 | 2.4 |

Example 3—Polymorph Screening

Polymorph screening for Compound 1 was conducted under different conditions, including anti-solvent addition, evaporation, slurry, solid/liquid vapor diffusion, crash cooling and grinding.

Slurry experiments were conducted at 4° C., RT and 50° C. in different solvent systems. For each experiment about 20 mg of Compound 1 Type A was suspended in 0.25-0.5 mL of solvent in a 1.5-mL glass vial. After the suspension was stirred for about one week at the desired temperature, the remaining solids were isolated for XRPD analysis. Results are summarized in Table 3-1.

TABLE 3-1

| Solvent, v/v | Temperature, ° C. | Solid Form |
|---|---|---|
| EtOH | RT | Type A |
| Acetone | RT | Type A |
| ACN | RT | Type A |
| 2-Me-THF/Heptane, 3:1 | RT | Type A |
| IPAc | RT | Type A |
| MTBE | RT/50 | Type A* |
| MIBK | RT/50 | Type A* |
| 1,4-Dioxane | RT | Type A |
| Toluene | RT | Type A |
| IPA | RT | Type A |
| Heptane | RT/50 | Type A* |
| $H_2O$ | RT/50 | Type A* |
| EtOH/$H_2O$, 3:7 aw = 0.8 | RT | Type A |
| EtOH/$H_2O$, 9:1 aw = 0.5 | RT | Type A |
| EtOH/$H_2O$, 95:5 aw = 0.3 | RT | Type A |
| EtOH/$H_2O$, 985:15 aw = 0.1 | RT | Type A |
| Cyclopentylmethylether | 4 | Type A |
| DMF | 4 | Type A** |
| ACN/$H_2O$, 3:1 | 4 | Type A |
| DCM | 4 | Type A |
| MeOH | RT | Type A |
| EtOAc | RT | Type A |

*Type A observed at both RT (one week) and 50° C. (four days)
**Clear solution obtained at 4° C. stirring and solids obtained from evaporation at RT Evaporation experiments were conducted under 12 conditions. For each experiment about 15 mg of Compound 1 Type A was dissolved in ~1.0 mL of solvent in a 1.5-mL glass vial. The resulting clear solutions were subjected to slow evaporation at RT to induce precipitation. The solids, if observed, were isolated for XRPD analysis. The results are summarized in Table 3-2.

TABLE 3-2

| Summary of evaporation experiments | |
|---|---|
| Solvent, v/v | Solid Form |
| ACN | Type A |
| MeOH | Type A |
| EtOAc | Amorphous |
| MEK | Type A |
| Acetone | Oil |
| DCM | Amorphous |
| THF | Amorphous |
| 1,4-Dioxane | Oil |
| Acetic acid | N/A |
| $CHCl_3$ | Amorphous |
| 2-Me-THF | Type A |
| MeOH/$H_2O$, 1:1 | Type A |

N/A: No solids obtained

A total of 8 anti-solvent addition experiments were carried out. About 5 mg of Compound 1 Type A was dissolved in 0.5-3.0 mL solvent to obtain a clear near saturated solution. 0.25-8.0 mL anti-solvent was then added to induce precipitation. The precipitate was isolated for XRPD analysis after stirring the resulting suspension overnight. Results are summarized in Table 3-3.

TABLE 3-3

| Solvent, v/v | Anti-solvent | Solid Form |
|---|---|---|
| MeOH | $H_2O$ | Type A |
| DMSO | $H_2O$ | Type A |

TABLE 3-3-continued

| Solvent, v/v | Anti-solvent | Solid Form |
|---|---|---|
| ACN | Heptane | N/A |
| THF | Heptane | Type A |
| EtOAc | Heptane | Type A |
| MEK | Heptane | Type A |
| Acetone | Heptane | Type A |
| DCM | Heptane | Type A |

N/A: no solid obtained

Both solid vapor diffusion and solution vapor diffusion methods were used. Two solid vapor diffusion experiments were conducted. For each one, approximately 30 mg of Compound 1 Type A sample was weighted into a 3-mL vial, which was then placed into a 20-mL vial containing 4 mL of volatile solvent. The 20-mL vial was sealed and kept at RT for about two weeks allowing sufficient time for organic vapor of the solvents to interact with the solid sample. The solids thus obtained were isolated for XRPD test. Five solution vapor diffusion experiments were conducted. Approximate 15-30 mg of Compound 1 Type A sample was dissolved in 2-4 mL of an appropriate solvent to obtain a saturated solution in a 5-mL vial. The solution was then placed into a 20-mL vial containing 4 mL of volatile solvents. The 20-mL vial was sealed and kept at RT for about two weeks allowing sufficient time for organic vapor of the anti-solvent to interact with the solution sample. The precipitates thus obtained were isolated for XRPD analysis. The results are summarized in Table 0-1 indicating no new form was observed.

TABLE 0-1

Summary of vapor diffusion experiments

| Method | Solvent, v/v | Anti-solvent | Solid Form |
|---|---|---|---|
| Solid vapor diffusion | $H_2O$ | N/A | Type A |
|  | DCM | N/A | Type A |
| Solution vapor diffusion | ACN | IPA | Amorphous |
|  | MeOH | Toluene | Type A |
|  | EtOAc | Heptane | Amorphous |
|  | Acetone | Toluene | Type A |
|  | THF | Heptane | Amorphous |

Example 4—Formulations of Compound 1 Type A

Compound 1 Type A can be formulated into a form (e.g., a capsule or unit dosage form) for oral use.

Compound 1 Type A was formulated into capsules as summarized in Table 4-1. Each encapsulated drug product excipient meets the requirements of the respective current United States Pharmacopeia (USP) or National Formulary (NF) monograph. As permitted under EMA/CHMP/QWP/834816/2015, reference is made to the current compendial monographs in lieu of inclusion of the current compendial specifications. The capsule shells, which consist of gelatin and about 2.9% w/w of titanium dioxide (E171), are specified according to the current compendial requirements for each ingredient. Each excipient may be obtained from qualified suppliers that meet the cited specifications, and may be accepted upon a supplier certificate of analysis with minimal confirmatory identification testing upon receipt and periodic confirmation of supplier results.

TABLE 4-1

| Dose Strength | Function | Component | Relative weight[2] |
|---|---|---|---|
| 50 mg or 150 mg | Active | Compound 1 Type A, Micronized[1] | 33.00 |
|  | Filler | Microcrystalline Cellulose NF/EP (Avicel PH101) | 61.12 |
|  | Disintegrant | Croscarmellose Sodium NF/EP | 4.95 |
|  | Lubricant | Magnesium Stearate NF/EP | 1.00 |
|  |  | Hard gelatin capsule shell, size 2 or size 00, white opaque | wt x |

[1]20% excess Compound 1 Type A was micronized to obtain sufficient material needed for the batch.
[2]As used herein, relative weights (or % w/w) are given as a percentage relative to the total weight of the formulation.

Compound 1 Type A was formulated into tablets or capsules as summarized in Table 4-2.

TABLE 4-2

| Component | Function | Formulation 1 (% w/w) | Formulation 2 (% w/w) | Formulation 3 (% w/w) | Formulation 4 (% w/w) |
|---|---|---|---|---|---|
| Compound 1 Type A | Active | 33.0 | 33.0 | 33.0 | 33.0 |
| Avicel PH101 (50 μm) | Filler | 61.0 | 0 | 49.0 | 49.0 |
| Avicel PH102 (100 μm) | Filler | 0.0 | 60.0 | 10.0 | 10.0 |
| Ac—Di-Sol | Disintegrant | 5.0 | 5.0 | 6.0 | 6.0 |
| Magnesium Stearate | Lubricant | 1.0 | 1.0 | 1.0 | 1.0 |
| Colloidal Silicon Dioxide | Glidant/anti-adherent/anti-static | 0.0 | 1.0 | 1.0 | 1.0 |

TABLE 4-2-continued

| Component | Function | Formulation 1 (% w/w) | Formulation 2 (% w/w) | Formulation 3 (% w/w) | Formulation 4 (% w/w) |
|---|---|---|---|---|---|
| Manufacturing Process | — | Dry blending | Dry blending | Dry granulation | Dry granulation |
| Final Dosage Form | — | Capsule | Capsule | Capsule | Tablet |

The invention claimed is:

1. A solid form of Compound 1:

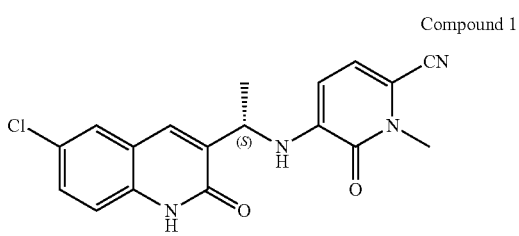

Compound 1 characterized by an X-ray Powder Diffraction (XRPD) pattern with a peak at angle (2 theta±0.2) of 6.3.

2. The solid form of claim 1, wherein the XRPD pattern further comprises a peak at angle (2 theta±0.2) of 5.7.

3. The solid form of claim 1 characterized by a differential scanning calorimetry (DSC) thermogram with an endothermic event observed at about 256.6° C.

4. An oral unit dosage form comprising, a solid form of (S)-5-((1-(6-chloro-2-oxo-1,2-dihydroquinolin-3-yl)ethyl)amino)-1-methyl-6-oxo-1,6-dihydropyridine-2-carbonitrile, wherein the solid form is characterized by an X-ray Powder Diffraction (XRPD) pattern with a peak at angle (2 theta±0.2) of 6.3, and
one or more excipients selected from the group consisting of a filler, a disintegrant, a lubricant, and a glidant.

5. The oral unit dosage form of claim 4, comprising a total of about 50-150 mg of the ((S)-5-((1-(6-chloro-2-oxo-1,2-dihydroquinolin-3-yl)ethyl)amino)-1-methyl-6-oxo-1,6-dihydropyridine-2-carbonitrile.

6. The oral unit dosage form of claim 4, comprising a total of about 150 mg of the ((S)-5-((1-(6-chloro-2-oxo-1,2-dihydroquinolin-3-yl)ethyl)amino)-1-methyl-6-oxo-1,6-dihydropyridine-2-carbonitrile.

7. The oral unit dosage form of claim 4, comprising a filler wherein the filler comprises microcrystalline cellulose.

8. The oral unit dosage form of claim 4, comprising a disintegrant, wherein the disintegrant comprises croscarmellose sodium.

9. The oral dosage unit of claim 4, comprising a glidant, wherein the glidant comprises colloidal silicon dioxide.

10. The oral dosage unit of claim 4, further comprising a lubricant.

11. The oral dosage unit of claim 10, wherein the lubricant comprises magnesium stearate.

12. The oral dosage unit of claim 4, wherein the (S)-5-((1-(6-chloro-2-oxo-1,2-dihydroquinolin-3-yl)ethyl)amino)-1-methyl-6-oxo-1,6-dihydropyridine-2-carbonitrile is about 33 percent by weight of the oral dosage unit.

13. The oral dosage unit of claim 10, wherein the (S)-5-((1-(6-chloro-2-oxo-1,2-dihydroquinolin-3-yl)ethyl)amino)-1-methyl-6-oxo-1,6-dihydropyridine-2-carbonitrile, the filler, the disintegrant and the lubricant are present in a relative weight ratio of about 33:61:5:1.

* * * * *